(12) United States Patent
Vleugels et al.

(10) Patent No.: US 11,069,443 B2
(45) Date of Patent: Jul. 20, 2021

(54) METHOD AND APPARATUS FOR TRACKING OF FOOD INTAKE AND OTHER BEHAVIORS AND PROVIDING RELEVANT FEEDBACK

(71) Applicant: MEDTRONIC MINIMED, INC., Northridge, CA (US)

(72) Inventors: Katelijn Vleugels, San Carlos, CA (US); Ronald Marianetti, II, Campbell, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 111 days.

(21) Appl. No.: 16/508,170

(22) Filed: Jul. 10, 2019

(65) Prior Publication Data

US 2019/0333634 A1    Oct. 31, 2019

Related U.S. Application Data

(63) Continuation of application No. 15/419,996, filed on Jan. 30, 2017, now Pat. No. 10,373,716.
(Continued)

(51) Int. Cl.
*G16H 40/63*    (2018.01)
*G16H 50/70*    (2018.01)
(Continued)

(52) U.S. Cl.
CPC .......... *G16H 40/63* (2018.01); *A61B 5/0022* (2013.01); *A61B 5/1118* (2013.01);
(Continued)

(58) Field of Classification Search
CPC ........ G16H 40/63; G16H 40/67; G16H 70/60; G16H 50/70; G16H 20/60; A61B 5/0022;
(Continued)

(56) References Cited

U.S. PATENT DOCUMENTS 9,042,596 B2 *   5/2015   Connor .................. G06K 9/228
                                                     382/100
9,254,099 B2 *   2/2016   Connor .................. G16H 20/60
(Continued)

FOREIGN PATENT DOCUMENTS

CN    101326526 A    12/2008
CN    102281817 A    12/2011

*Primary Examiner* — Michael Tomaszewski
(74) *Attorney, Agent, or Firm* — Lorenz & Kopf, LLP

(57) ABSTRACT

A sensing device monitors and tracks food intake events and details. A processor, appropriately programmed, controls aspects of the sensing device to capture data, store data, analyze data and provide suitable feedback related to food intake. More generally, the methods might include detecting, identifying, analyzing, quantifying, tracking, processing and/or influencing, related to the intake of food, eating habits, eating patterns, and/or triggers for food intake events, eating habits, or eating patterns. Feedback might be targeted for influencing the intake of food, eating habits, or eating patterns, and/or triggers for those. The sensing device can also be used to track and provide feedback beyond food-related behaviors and more generally track behavior events, detect behavior event triggers and behavior event patterns and provide suitable feedback.

30 Claims, 16 Drawing Sheets

Related U.S. Application Data

(60) Provisional application No. 62/288,408, filed on Jan. 28, 2016.

(51) Int. Cl.
| | | |
|---|---|---|
| *G16H 20/60* | (2018.01) | |
| *A61B 5/16* | (2006.01) | |
| *G16H 70/60* | (2018.01) | |
| *A61B 5/00* | (2006.01) | |
| *A61B 5/11* | (2006.01) | |
| *G16H 40/67* | (2018.01) | |

(52) U.S. Cl.
CPC ......... *A61B 5/1121* (2013.01); *A61B 5/1123* (2013.01); *A61B 5/16* (2013.01); *A61B 5/4866* (2013.01); *A61B 5/4875* (2013.01); *A61B 5/7282* (2013.01); *G16H 20/60* (2018.01); *G16H 40/67* (2018.01); *G16H 50/70* (2018.01); *G16H 70/60* (2018.01); *A61B 2505/07* (2013.01); *A61B 2560/0209* (2013.01); *A61B 2562/0219* (2013.01)

(58) Field of Classification Search
CPC ... A61B 5/1118; A61B 5/1121; A61B 5/1123; A61B 5/16; A61B 5/4866; A61B 5/4875; A61B 5/7282; A61B 2505/07; A61B 2560/0209; A61B 2562/0219
USPC ........................................................ 705/2–3
See application file for complete search history.

(56) References Cited

U.S. PATENT DOCUMENTS

| | | | | |
|---|---|---|---|---|
| 9,442,100 | B2* | 9/2016 | Connor | G16H 20/60 |
| 9,529,385 | B2* | 12/2016 | Connor | G06F 1/163 |
| 9,536,449 | B2* | 1/2017 | Connor | G16H 20/60 |
| 2002/0022774 | A1 | 2/2002 | Karnieli | |
| 2009/0012433 | A1 | 1/2009 | Fernstrom et al. | |
| 2010/0188328 | A1* | 7/2010 | Dodge | G06F 3/04883 345/156 |
| 2010/0194573 | A1* | 8/2010 | Hoover | A61B 5/681 340/573.1 |
| 2014/0347491 | A1 | 11/2014 | Connor | |
| 2014/0349256 | A1* | 11/2014 | Connor | A47G 21/02 434/127 |
| 2015/0379238 | A1* | 12/2015 | Connor | G16H 20/60 702/19 |
| 2016/0073953 | A1* | 3/2016 | Sazonov | A61B 5/1107 600/590 |
| 2016/0132642 | A1* | 5/2016 | Carmi | G06F 3/017 348/77 |

* cited by examiner

METHOD AND APPARATUS FOR TRACKING OF FOOD INTAKE AND OTHER BEHAVIORS AND PROVIDING RELEVANT FEEDBACK

CROSS-REFERENCES TO PRIORITY AND RELATED APPLICATIONS

This application is a continuation of U.S. patent application Ser. No. 15/419,996, filed Jan. 30, 2017 and issued on Aug. 6, 2019 as U.S. Pat. No. 10,373,716, entitled "Method and Apparatus for Tracking of Food Intake and Other Behaviors and Providing Relevant Feedback," which claims priority from U.S. Provisional Patent Application No. 62/288,408 filed Jan. 28, 2016, entitled "Method and Apparatus for Food Intake Tracking and Feedback." The entire disclosures of applications recited above are hereby incorporated by reference, as if set forth in full in this document, for all purposes.

FIELD OF THE INVENTION

The present invention relates generally to electronic devices that relate to health technology and more particularly to methods and apparatus for using sensors for tracking a person's food intake, a processor for analyzing a food intake process and electronic circuits for providing feedback to the person. The methods and apparatus can extend beyond just food intake.

BACKGROUND

Diet-related health issues have become one of the top global public health issues. In the past couple of decades, there has been a dramatic surge in obesity and other diet-related health issues. According to the Center for Disease Control (CDC), in 2011-2012 69% of all American adults age 20 and over were overweight and more than one third of American adults were obese. Obesity can lead to many health issues such as for example cardiovascular diseases, Type 2 diabetes, hypertension, cancers, respiratory problems, gallbladder disease and reproductive complications. While there may be multiple factors leading to or contributing to obesity, one critical factor is a person's behavior as it relates to food intake.

Over the years, several attempts have been made to track food and nutrition intake. One common way for a person to track their food intake is to maintain a written diary. There are several issues with this approach. First of all, the accuracy of human-entered information tends to be limited. Secondly, maintaining a written diary is cumbersome and time-consuming, causing many users to drop out after a short period of time. Thirdly, there is no mechanism for real-time feedback. Fourthly, they do not provide any insights into important aspects of eating behavior, such as the pace of eating.

More recently, software, typically installed on or accessed from a tablet, mobile phone, laptop or computer, can be used to facilitate the logging and tracking of a person's food intake. Such software applications typically utilize a database that contains nutrient and caloric information for a large number of food items. Unfortunately, devices and software to facilitate food journaling are often times cumbersome to use and require a lot of human intervention, such as manual data entry or look up. They are furthermore mostly focused on food intake content and portion tracking and do not provide insight into other aspects of eating behavior such as the number of bites or the pace of eating. They also lack the ability to provide real-time feedback about eating habits or behavior.

Devices and methods that attempt to reduce the burden of manual data entry or data look-up exist and provide another approach to obtaining log data about food consumption. As an example, tableware and utensils with built-in sensors have been proposed to track food intake more automatically. For example, a plate with integrated sensors and circuitry might automatically quantify and track the content of food that is placed on the plate. Similarly, integrated sensors in a drinking vessel might identify, quantify and track the contents of liquid in the cup. In another example, an eating utensil includes sensors that count the number of bites taken by a person using the eating utensil. These methods might fall short in not being able to automatically identify and quantify the content of the food being consumed and also only apply to a limited set of meal scenarios and dining settings and are not well suited to properly cover the wide range of different meal scenarios and dining settings that a typical person may encounter during a day.

Being able to handle a wide variety of meal scenarios and settings is important for seamless and comprehensive food intake tracking. A method based on an eating utensil may not be able to properly track the intake of drinks, snacks or finger foods and such methods may also interfere with a person's normal social behavior. For example, it might not be socially acceptable for a user to bring their own eating utensils to a restaurant or a dinner at a friend's house.

Devices and methods have been described that quantify and track food intake based on analysis of images of food taken by a portable device that has imaging capabilities, such as an app that runs on a mobile phone or tablet that has a camera. Some devices might use spectroscopy to identify food items based on their molecular makeup. Such devices may use crowd sourcing and/or computer vision techniques, sometimes complemented with other image processing techniques, to identify a food item, estimate its nutritional content and/or estimate its portion size. However, many of these devices and methods are fond lacking in usability and availability in certain social settings.

While today's spectroscopy technology has been sufficiently miniaturized to be included in portable devices, devices based on spectroscopy do have a number of significant issues. First of all, such devices require a significant amount of human intervention and cannot be easily used in a discreet way. In order to produce an accurate spectrograph measurement, the person eating is required to hold the spectrometer for a few seconds close to or in contact with each food item they desire to identify. Since the light generated by such portable spectrometers can only penetrate up to a few centimeters into the food, multiple measurements are required for food items that do not have a homogeneous composition and thus a portable spectrometer would not work well for sandwiches, layered cakes, mixed salads, etc. Such human intervention is intrusive to the dining experience and may not be acceptable in many dining settings.

Improved methods and apparatus for food intake monitoring and analysis are needed.

SUMMARY

A sensing device monitors and tracks food intake events and details. A processor, appropriately programmed, controls aspects of the sensing device to capture data, store data, analyze data and provide suitable feedback related to food intake. More generally, the methods might include detecting, identifying, analyzing, quantifying, tracking, processing and/or influencing, related to the intake of food, eating habits, eating patterns, and/or triggers for food intake events, eating habits, or eating patterns. Feedback might be targeted for influencing the intake of food, eating habits, or eating patterns, and/or triggers for those. The sensing device can also be used to track and provide feedback beyond food-related behaviors and more generally track behavior events, detect behavior event triggers and behavior event patterns and provide suitable feedback.

The following detailed description together with the accompanying drawings will provide a better understanding of the nature and advantages of the present invention.

BRIEF DESCRIPTION OF THE DRAWINGS

Various embodiments in accordance with the present disclosure will be described with reference to the drawings, in which.

DETAILED DESCRIPTION

Figure 1:
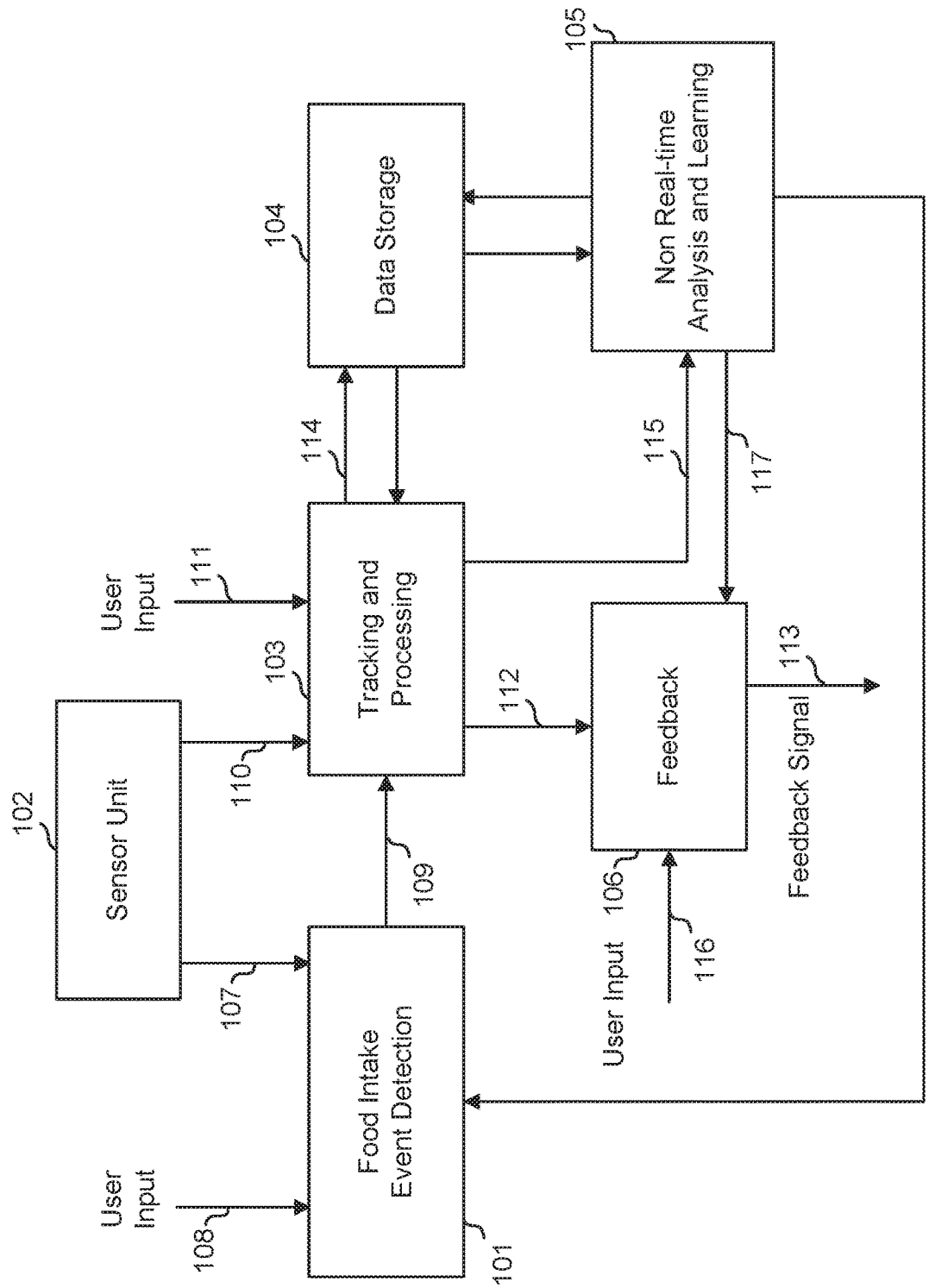
FIG. 1 is an illustrative example of an environment in accordance with at least one embodiment.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Various examples are provided herein of devices that a person would use to monitor, track, analyze and provide feedback on food intake, the intake process and timing and other relevant aspects of a person's eating, drinking and other consumption for various ends, such as providing diet information and feedback. The data related to food intake process might include, timing of the eating process, pace of eating, time since last food intake event, what is eaten, estimates of the contents of what is eaten, etc. While a lot of the examples described herein are related to food intake events, the methods and devices described herein are also applicable to other behavior events such as brushing teeth, smoking, biting nails, etc. Data can be obtained from some stationary device having sensors and electronics, some mobile device having sensors and electronics that is easily moved and carried around by a person, and/or from wearable devices having sensors and electronics that a person attaches to their person or clothing, or is part of the person's clothing. In general, herein such devices are referred to as sensing devices. Herein, the person having such a device and who's consumption is being monitored is referred to as the user but it should be understood that the device might be used unchanged in situations where the person consuming, the person monitoring, and the person evaluating feedback need not all be the same person. Herein, what is consumed is referred to as food intake, but it should be clear that these devices can be used to more generally track consumption and consumption patterns. A behavior tracking/feedback system as described herein might comprise one or more wearable devices and might also comprise one or more additional devices that are not worn. These additional devices might be carried by the wearer or kept nearby so that they can communicate with the wearable devices. The behavior tracking/feedback system might also comprise remote elements, such as a remote cloud computing element and/or remote storage for user information.

A wearable device might be worn at different locations on the wearer's body (i.e., the person monitoring their behavior) and the wearable device might be programmed or configured to account for those differences, as well as differences from wearer to wearer. For example, a right-handed person may wear the device around his right wrist whereas a left-handed person may wear the device around his left wrist. Users may also have different preferences for orientation. For example, some users may want the control buttons on one side, whereas other users may prefer the control buttons on the opposite side. In one embodiment, the user may manually enter the wrist preference and/or device orientation.

In another embodiment, the wrist preference and/or device orientation may be determined by asking the user to perform one or more pre-defined gestures and monitoring the sensor data from the wearable device corresponding to the user performing the pre-defined gesture or set of gestures. For example, the user may be asked to move his hand towards his mouth. The change in accelerometer sensor readings across one or more axes may then be used to determine the wrist and device orientation. In yet another example, the behavior tracking/feedback system may process the sensor readings from the wearable device while the user is wearing the device for a certain duration of time.

Optionally, the behavior tracking/feedback system may further combine the sensor readings with other data or metadata about the wearer, to infer the wrist and device orientation. For example, the behavior tracking/feedback system may monitor the user for one day and record the accelerometer sensor readings across one or more of the axes.

Since the movement of the lower arm is constrained by the elbow and upper arm, some accelerometer readings will be more frequent than others based on the wrist and device orientation. The information of the accelerometers can then be used to determine the wrist and/or device orientation. For example, the mean, minimum, maximum and/or standard deviation of the accelerometer readings could be used to determine the wrist and/or device orientation.

In some embodiments, sensing devices can sense, without requiring user interaction, the start/end of a food intake event, the pace of eating, the pace of drinking, the number of bites, the number of sips, the estimation of fluid intake, and/or estimation of portion sizing. Operating with less human intervention, no human intervention, or only intervention not apparent to others will allow the devices to scale well with different meal scenarios and different social situations. Sensing might include capturing details of the food before it is consumed, as well as user actions that are known to accompany eating, such as repeated rotation of an upper arm or other hand-to-mouth motions. Sensors might include an accelerometer, a gyroscope, a camera, and other sensors.

Using the devices can provide a person with low friction-of-use to detect, quantify, track and provide feedback related to the person's food intake content as well as the person's food intake behavior. Such methods have the potential of preventing, treating and, in certain cases, even curing diet-related diseases. Such devices can improve efficacy, accuracy and compliance, and reduce the burden of usage and to improve social acceptance. The devices can operate autonomously with no, or very minimal, human intervention, and do not interfere in an invasive or otherwise significant negative way with a person's normal activities or social interactions or intrude on the person's privacy. The devices are able to handle a wide range of meal scenarios and dining settings in a discreet and socially-acceptable manner, and are capable of estimating and tracking food intake content and quantity as well as other aspects of eating behavior. The devices can provide both real-time and non-real-time feedback to the person about their eating behavior, habits and patterns.

It is generally known and understood that certain eating behaviors can be linked to, triggered by or otherwise be influenced by physical, mental or environmental conditions such as for example hunger, stress, sleep, addiction, illness, physical location, social pressure, and exercise. These characteristics can form inputs to the processing performed by or for the devices.

The devices might be useful for a person concerned about their diet. For example, people with Type 1 diabetes are usually on an insulin therapy where, based on their food intake and other factors, they administer the proper insulin dosage. While the cause of Type 1 diabetes may not be directly linked to a person's eating behavior, a person with Type 1 diabetes needs to carefully track his or her food intake in order to manage his or her insulin therapy. Such patients will also benefit from easier to use and more discreet methods for food intake tracking. In some embodiments of the sensing devices, the sensing device is part of a feedback-driven automated insulin delivery therapy system. Such a system might include continuous monitoring of a patient's glucose levels, a precision insulin delivery system, and the use of insulin that has a faster absorption rate, that would further benefit from information that can be extracted from automated and seamless food intake tracking, such as the tracking of carbohydrates and sugar intake. The devices might also be useful for wellness programs and the like.

A food intake event generally relates to a situation, circumstance or action whereby a person eats, drinks or otherwise takes into his or her body an edible substance. Edible substances may include, but are not limited to, solid foods, liquids, soups, drinks, snacks, medications, vitamins, drugs, herbal supplements, finger foods, prepared foods, raw foods, meals, appetizers, main entrees, desserts, candy, breakfast, sports or energy drinks. Edible substances include, but are not limited to, substances that may contain toxins, allergens, viruses, bacteria or other components that may be harmful to the person, or harmful to a population or a subset of a population. Herein, for readability, food is used as an example of an edible substance, but it should be understood that other edible substance might be used instead of food unless otherwise indicated.

Eating habits and patterns generally relate to how people consume food. Eating habits and patterns may include, but are not limited to, the pace of eating or drinking, the size of bites, the amount of chewing prior to swallowing, the speed of chewing, the frequency of food intake events, the amount of food consumed during a food intake event, the position of the body during a food intake event, possible movements of the body or of specific body parts during the food intake event, the state of the mind or body during a food intake event, and the utensils or other devices used to present, handle or consume the food. The pace of eating or drinking might be reflected in the time between subsequent bites or sips.

Triggers generally relate to the reasons behind the occurrence of a food intake event, behind the amount consumed and behind how it is consumed. Triggers for food intake events and for eating habits or patterns may include, but are not limited to, hunger, stress, social pressure, fatigue, addiction, discomfort, medical need, physical location, social context or circumstances, odors, memories or physical activity. A trigger may coincide with the food intake event for which it is a trigger. Alternatively, a trigger may occur outside the food intake event window, and might occur prior to or after the food intake event at a time that may or may not be directly related to the time of the food intake event.

In some embodiments of the sensing device or system, fewer than all of the features and functionality presented in this disclosure are implemented. For example, some embodiments may focus solely on detection and/or processing and tracking of the intake of food without intending to steer the user to modify his or her food intake or without tracking, processing or steering eating habits or patterns.

In many examples herein, the setting is that an electronic device is provided to a user, who wears the electronic device, alone or while it is in communication with a nearby support device that might or might not be worn, such as a smartphone for performing operations that the worn electronic device offloads. In such examples, there is a person wearing the electronic device and that person is referred to as the "wearer" in the examples and the system comprises a worn device and may include other components that are not worn and are nearby and components that are remote, preferably able to communicate with the worn device. Thus, the wearer wears the electronic device, the electronic device includes sensors, which sense environment about the wearer. That sensing can be of ambient characteristics, body characteristics, movement and other sensed signals as described elsewhere herein.

In many examples, functionality of the electronic device might be implemented by hardware circuitry, or by program instructions that are executed by a processor in the electronic device, or a combination. Where it is indicated that a processor does something, it may be that the processor does that thing as a consequence of executing instructions read from an instruction memory wherein the instructions provide for performing that thing. While other people might be involved, a common example here is where the wearer of the electronic device is using that electronic device to monitor their own actions, such as gestures, behavior events comprising a sequence of gestures, activities, starts of activities or behavior events, stops of activities or behavior events, etc. Where it is described that a processor performs a particular process, it may be that part of that process is done separate from the worn electronic device, in a distributed processing fashion. Thus, a description of a process performed by a processor of the electronic device need not be limited to a processor within the worn electronic device, but perhaps a processor in a support device that is in communication with the worn electronic device.

FIG. 1 shows a high level functional diagram of a dietary tracking and feedback system in accordance with an embodiment of the present invention. A system for dietary tracking and feedback may in part include one or more of the following: a food intake event detection subsystem 101, one or more sensors 102, a tracking and processing subsystem 103, a feedback subsystem 106, one or more data storage units 104 and a learning subsystem that might perform non-real-time analysis. In some embodiments, elements shown in FIG. 1 are implemented in electronic hardware, while in others some elements are implemented in software and executed by a processor. Some functions might share hardware and processor/memory resources and some functions might be distributed. Functionality might be fully implemented in a sensor device, or functionality might be implemented across the sensor device, a processing system that the sensor device communicates with, such as a smartphone, and/or a server system that handles some functionality remote from the sensor device. For example, a wearable sensor device might make measurements and communicate them to a mobile device, which then uploads them over the Internet to a server that further processes the data. Data or other information may be stored in a suitable format, distributed over multiple locations or centrally stored, in the form recorded, or after some level of processing. Data may be stored temporarily or permanently.

A first component of the system illustrated in FIG. 1 is the food intake event detection subsystem 101. The role of this subsystem is to identify the start and/or end of a food intake event and communicate an actual, probable or imminent occurrence of the start and/or end of a food intake event to other components in the system.

In general, the device detects what could be the start of a food intake event or the probable start of a food intake event, but the device would work sufficient for its purposes so long as the device reasonably determines such start/probable start. For clarity, that detection is referred to as a "deemed start" of a food intake event and when various processes, operations and elements are to perform some action or behavior in connection with the start of a food intake event, it would be acceptable for those various processes, operations and elements to take a deemed start as the start even if occasionally the deemed start is not in fact a start of a food intake event.

In one embodiment, the detection and/or signaling of the occurrence of the deemed start of a food intake event coincides with the deemed start of a food intake event. In another embodiment, it may occur sometime after the deemed start of the food intake event. In yet another embodiment, it may occur sometime before the deemed start of the food intake event. It is usually desirable that the signaling is close to the deemed start of the food intake event. In some embodiments of the current disclosure, it may be beneficial that the detection and/or signaling of the deemed start of a food intake event occurs ahead of the start of said food intake event. This may for example be useful if a message or signal is to be sent to the user, a healthcare provider or caregiver ahead of the start of the food intake event as a coaching mechanism to help steer a user's food intake decisions or eating habits.

In a preferred embodiment of the present disclosure, the detection of the start and/or ending of a food intake event by the food intake event detection subsystem 101 happens autonomously and does not require any special user intervention. To accomplish this, the food intake event detection subsystem may use inputs 107 from one or more sensors 102. Sensors may include, but are not limited to, accelerometers, gyroscopes, magnetometers, magnetic angular rate and gravity (MARG) sensors, image sensors, cameras, optical sensors, proximity sensors, pressure sensors, odor sensors, gas sensors, glucose sensors, Global Positioning Systems (GPS), and microphones.

Methods for autonomous detection may include, but are not limited to, detection based on monitoring of movement or position of the body or of specific parts of the body, monitoring of arm movement, position or gestures, monitoring of hand movement, position or gestures, monitoring of finger movement, position or gestures, monitoring of swallowing patterns, monitoring of mouth and lips movement, monitoring of saliva, monitoring of movement of cheeks or jaws, monitoring of biting or teeth grinding, monitoring of signals from the mouth, the throat and the digestive system. Methods for detection may include visual, audio or any other types of sensory monitoring of the person and/or his or her surroundings. The monitored signals may be generated by the dietary tracking and feedback system. Alternatively, they may be generated by a separate system but be accessible to the dietary tracking and feedback system through an interface. Machine learning and other data analytics techniques may be applied to detect the start or probable start of a food intake event from the input signals being monitored.

In one example, the food intake detection system 101 may monitor the outputs of accelerometer and/or gyroscope sensors to detect a possible bite gesture or a possible sip gesture. Such gestures might be determined by a gesture processor that uses machine learning to distill gestures from sensor readings. The gesture processor might be part of the processor of the worn device or in another part of the system.

Gesture detection machine learning techniques as described elsewhere herein may be used to detect a bite gesture or sip gesture, but other techniques are also possible. The food intake detection system 101 may further assign a confidence level to the detected bite gesture or sip gesture. The confidence level corresponds to the likelihood that the detected gesture is indeed a bite or sip gesture. The food intake detection system may determine that the start of a food intake event has occurred based on the detection of a gesture and its confidence level without any additional inputs. For example, the food intake event detection system 101 may decide that the start of a food intake event has occurred when the confidence level of the bite or sip gesture exceeds a pre-configured threshold.

Alternatively, when a possible bite or sip gesture has been detected, the food intake event detection system 101 may use additional inputs to determine that the start or probable start of a food intake event has occurred. In one example, the food intake event detection system 101 may monitor other gestures that are close in time to determine if the start of a food intake event has occurred. For example, upon detection of a possible bite gesture, the food intake event detection system 101 may wait for the detection of another bite gesture within a certain time window following the detection of the first gesture and/or with a certain confidence level before determining that the start of a food intake event had occurred.

Upon such detection, the food intake detection system 101 may place one or more circuits or components into a higher performance mode to further improve the accuracy of the gesture detection. In another example, the food intake event detection system 101 may take into consideration the time of the day, or the location of the user to determine if the start or probable start of a food intake event has taken place. The food intake event detection system may use machine learning or other data analytics techniques to improve the accuracy and reliability of its detection capabilities. For example, training data obtained from the user and/or from other users at an earlier time may be used to train a classifier. Training data may be obtained by asking for user confirmation when a possible bite or sip gesture has been detected. A labeled data record can then be created and stored in memory readable by the gesture processor that includes the features related to the gesture, along with other contextual features, such as time of day or location. A classifier can then be trained on a labeled dataset comprised of multiple labeled data records set of labeled data records, and the trained classifier model can then be used in a food intake event detection system to more accurately detect the start of a food intake event.

In another embodiment, the food intake detection subsystem may use triggers to autonomously predict the probable start of a food intake event. Methods for autonomous detection of a probable start of a food intake event based on triggers may include, but are not limited to, monitoring of a person's sleep patterns, monitoring of a person's stress level, monitoring of a person's activity level, monitoring of a person's location, monitoring of the people surrounding a person, monitoring of a person's vital signs, monitoring of a person's hydration level, monitoring of a person's fatigue level. In some cases, the food intake detection subsystem may monitor one or more specific trigger signals or trigger events over a longer period of time and, in combination with the non-real-time analysis and learning subsystem 105 apply machine learning or other data analytics techniques to predict the probable occurrence of a start of a food intake event.

For example, without any additional information, it can be very difficult to predict when a user will eat breakfast. However, if the system has a record over a number of days of the user's wake up time and the day of the week, the system can use that historical pattern in determining a likely time for the user to eat breakfast. Those records might be determined by the system, possibly with feedback from the user about their accuracy or those records might be determined by the user and input via a user interface of the system. The user interface might be the worn device itself or, for example, a smartphone app. As a result, the system can process correlations in the historical data to predict the time or time window that the user is most likely to have breakfast based on the current day of week and at what time the user woke up. Other trigger signals or trigger events may also be used by the non-real-time analysis and learning subsystem 105 to predict the time that a user will eat breakfast.

In another example, the non-real-time analysis and learning system 105 may, over a certain period of time record the stress level of a user. The stress level may, for example, be determined by monitoring and analyzing the user's heart rate or certain parameters related to the user's heart rate. The stress level may also be determined by analyzing a user's voice. The stress level may also be determined by analyzing the content of a user's messages or electronic communication. Other methods for determining the stress level are also possible. The non-real-time analysis and learning system 105 may furthermore, over the same period of time, record the occurrence of food intake events and certain characteristics of the food intake event such as the pace of eating, the quantity of food consumed, the time spacing between food intake events etc. It may then be possible by analyzing the historical data of stress levels, the occurrence of food intake events and food intake event characteristics and by looking at correlations in the historical data of stress levels, the occurrence of food intake events and food intake event characteristics, to predict based on the current stress level the probability that a user will start a food intake event in a certain time window in the future, or predict what time window in the future, the user will be most likely to start a food intake event. It may also be possible to predict characteristics of said food intake event, such as for example pace of eating or quantity of consumption.

In specific embodiments, the non-real time analysis and learning subsystem may use historical data from different users, or a combination of data from other users and from the wearer, and use similarities between one or more of the different users and the wearer, such as age, gender, medical conditions, etc. to predict the probable start of a food intake event by the wearer.

In yet other examples, the non-real-time analysis and learning subsystem 105 may use methods similar to the methods described herein to predict when a user is most likely to relapse in a binge eating episode or is most likely to start convenience snacking.

A variety of sensors may be used for such monitoring. The monitored signals may be generated by the dietary tracking and feedback system. Alternatively, they may be generated by a separate system but be accessible to the dietary tracking and feedback system for processing and/or use as trigger signals. Machine learning and other data analytics techniques may also be applied to predict some other characteristics of the probable intake event, such as the type and/or amount of food that will likely be consumed, the pace at which a person will likely be eating, the level of satisfaction a person will have from consuming the food, etc.

The machine learning process performed as part of gesture recognition might use external data to further refine its decisions. This might be done by non-real-time analysis and learning subsystem process. The data analytics process might, for example, consider the food intake events detected by the gesture-sensing based food intake detection system and the gesture-sensing based tracking and processing system, thus forming a second layer of machine learning. For example, over a period of time, food intake events and characteristics related to those food intake events are recorded, such as eating pace, quantity of food consumption, food content, etc., while also tracking other parameters that are not directly, or perhaps not obviously, linked to the food intake event. This could be, for example, location information, time of day a person wakes up, stress level, certain patterns in a person's sleeping behavior, calendar event details including time, event location and participant lists, phone call information including time, duration, phone number, etc., email metadata such as time, duration, sender, etc. The data analytics process then identifies patterns and correlations. For example, it may determine a correlation between the number of calendar events during the day and the characteristics of the food intake event(s) in the evening. This might be due to the user being more likely to start snacking when arriving home, or that dinner is larger and/or more rushed when the number of calendar event(s) for that day exceeds a certain threshold. With subsystem 105, it becomes possible to predict food intake events and characteristics from other signals and events that are not obviously linked to food intake.

Processing and analysis of one or more sensor inputs, and/or one or more images over longer periods of time, optionally using machine learning or other data analytics techniques may also be used to estimate the duration of a food intake event or may be used to predict that the end of a food intake event is probable or imminent.

In another embodiment, some user input 108 may be necessary or desirable to properly or more accurately detect the start and/or end of a food intake event. Such user input may be provided in addition to external inputs and inputs received from sensors 102. Alternatively, one or more user inputs may be used instead of any sensor inputs. User inputs may include, but are not limited to activating a device, pressing a button, touching or moving a device or a specific portion of a device, taking a picture, issuing a voice command, making a selection on a screen or entering information using hardware and/or software that may include but is not limited to a keyboard, a touchscreen or voice-recognition technology. If one or more user inputs are required, it is important that the user interaction is conceived and implemented in a way that minimizes the negative impact on a person's normal activities or social interactions.

A food intake event detection subsystem may combine multiple methods to autonomously detect predict the actual, probably or imminent start and/or end of a food intake event.

Another component of the system is the tracking and processing subsystem 103. In a preferred embodiment of the present disclosure, this subsystem interfaces 109 with the food intake event detection subsystem 101, and gets activated when it receives a signal from the food intake event detection subsystem that the actual, probable or imminent start of an event has been detected, and gets disabled when or sometime after it receives a signal from the food intake event detection subsystem that the actual, probable or imminent ending of an event has been detected. Upon detection of the start of a food intake event, the device might trigger activation of other sensors or components of the food intake tracking system, and might also trigger the deactivation of those upon detection of the end of the food intake event.

In another embodiment of the current disclosure, the tracking and processing subsystem may be activated and/or deactivated independent of any signals from the food intake detection subsystem. It is also possible that certain parameters be tracked and/or processed independently of any signals from the food intake detection subsystem, whereas the tracking and/or processing of other parameters may only be initiated upon receiving a signal from the food intake event detection subsystem.

The tracking and processing subsystem usually involves collecting data over an interface 110 from one or more sensors 102 and processing that data to extract relevant information. The sensor inputs may be the same or similar to the inputs sent to the food intake event detection subsystem. Alternatively, different and/or additional sensor inputs may be collected. Sensors may include, but are not limited to, accelerometers, gyroscopes, magnetometers, image sensors, cameras, optical sensors, proximity sensors, pressure sensors, odor sensors, gas sensors, Global Positioning Systems (GPS) circuit, microphones, galvanic skin response sensors, thermometers, ambient light sensors, UV sensors, electrodes for electromyographic ("EMG") potential detection, bio-impedance sensors, spectrometers, glucose sensors, touchscreen or capacitive sensors. Examples of sensor data include motion data, temperature, heart rate, pulse, galvanic skin response, blood or body chemistry, audio or video recording and other sensor data depending on the sensor type. The sensor inputs might be communicated to a processor wirelessly or via wires, in analog or digital form, intermediated by gating and/or clocking circuits or directly provided.

Processing methods used by the tracking and processing subsystem may include, but are not limited to, data manipulation, algebraic computation, geo-tagging, statistical computing, machine learning, computer vision, speech recognition, pattern recognition, compression and filtering.

Collected data may optionally be temporarily or permanently stored in a data storage unit 104. The tracking and processing subsystem 103 may use its interface 114 to the data storage unit 104 to place data or other information in the data storage unit 104 and to retrieve data or other information from the data storage unit 104.

In a preferred embodiment of the present disclosure, the collection of data, processing and tracking happen autonomously and do not require any special user intervention. Tracked parameters may include, but are not limited to, the following: location, temperature of surroundings, ambient light, ambient sounds, biometric information, activity levels, image captures of food, food names and descriptions, portion sizes, fluid intake, caloric and nutrient information, counts of mouthfuls, bite counts, sip counts, time durations between consecutive bites or sips, and duration of food intake events. Tracked parameters may also include, for each bite or sip, the time duration that the user's hand, arm and/or utensil is near the user's mouth, the time duration that the content of the bite or sip resides in the user's mouth before swallowing. The methods may vary based on what sensor data is available.

In other embodiments of the present disclosure, some user intervention 111 is required or may be desirable to achieve for example greater accuracy or input additional detail. User interventions 111 may include, but are not limited to, activating a device or specific functionality of a device, holding a device in position, taking pictures, adding voice annotations, recording video, making corrections or adjustments, providing feedback, doing data entry, taking measurements on food or on food samples. Measurements may include, but are not limited to, non-destructive techniques such as for example obtaining one or more spectrographs of food items, or chemistry methods that may require a sample taken from the food.

The processing of sensor data and user inputs by the tracking and processing subsystem 103 usually occurs real-time or near real-time. There may be some delays, for example to conserve power or to work around certain hardware limitations, but in some embodiments, the processing occurs during the food intake event, or in case of tracking outside of a food intake event, around the time that the sensor or user inputs have been received.

In certain implementations or under certain circumstances, there may not be real-time or near real-time access to the processing unit required to perform some or all of the processing. This may, for example, be due to power consumption or connectivity constraints. Other motivations or reasons are also possible. In that case, the inputs and/or partially processed data may be stored locally until a later time when access to the processing unit becomes available.

In one specific embodiment of the present disclosure, sensor signals that track movement of a person's arm, hand or wrist may be sent to the tracking and processing subsystem. The tracking and processing subsystem may process and analyze such signals to identify that a bite of food or sip of liquid has been consumed or has likely been consumed by said person. The tracking and processing subsystem may furthermore process and analyze such signals to identify and/or quantify other aspects of eating behavior such as for example the time separation between bites or sips, the speed of hand-to-mouth movement etc. The tracking and processing subsystem may furthermore process and analyze such signals to identify certain aspects of the eating method such as, for example, whether the person is eating with a fork or spoon, is drinking from a glass or can, or is consuming food without using any utensils.

In a specific example, it might be that the wearer rotates his or her wrist in one direction when bringing an eating utensil or hand to the mouth when taking a bite, but rotates in the other direction when sipping a liquid. The amount of rotation of a wearer's wrist as he or she moves his or her wrist to the mouth or away from the mouth and the duration that the wrist is held at a higher rotation angle may also be different for a drinking gesture versus an eating gesture. Other metrics may be used to distinguish eating gestures from drinking gestures or to distinguish differences in eating methods. A combination of multiple metrics may also be used. Other examples of metrics that may be used to distinguish eating gestures from drinking gestures or to distinguish differences in eating methods include but are not limited to the change in angle of the roll from the start or approximate start of the gesture until the time or approximate time that the hand reaches the mouth, the change in angle of the roll from the time or approximate time that the hand is near the mouth until the end or approximate end of the gesture, the variance of accelerometer or gyroscope readings across one or more of the axes for a duration of time when the hand is near the mouth, or for a duration of time that is centered around when the hand is near the mouth, or for a duration of time that may not be centered around when the hand is near the mouth but that includes the time when the hand is the nearest to the mouth, the variance of the magnitude of the accelerometer readings for a duration of time when the hand is near the mouth, or for a duration of time that is centered around when the hand is the nearest to the mouth, or for a duration of time that may not be centered around when the hand is the nearest to the mouth but that includes the time when the hand is the nearest to the mouth, the maximum value of the magnitude of the accelerometer readings for a duration of time when the hand is near the mouth, or for a duration of time that is centered around when the hand is the nearest to the mouth, or for a duration of time that may not be centered around when the hand is the nearest to the mouth but that includes the time when the hand is the nearest to the mouth. The magnitude of the accelerometer reading may be defined as square root of the acceleration in each orthogonal direction (e.g., sense acceleration in the x, y, and z directions and calculate $SQRT(a_x^2+a_y^2+a_z^2)$).

The position of the hand vis-à-vis the mouth can, for example, be determined by monitoring the pitch or the worn device and from there the pitch of the wearer's arm. The time corresponding to the peak of the pitch could be used as the moment in time when the hand is the nearest to the mouth. The time when the pitch starts rising could, for example, be used as the start time of the gesture. The time when the pitch stops falling could for example be used as the end time of the gesture.

Other definitions for nearest mouth position, start of movement and end of movement are also possible. For example, the time when the roll changes direction could be used instead to determine the time when the arm or hand is the nearest to the mouth. The time when the roll stops changing in a certain direction or at a certain speed could be used instead to determine the start time of the movement towards the mouth.

The tracking and processing subsystem may furthermore process and analyze such signals to determine appropriate or preferred times to activate other sensors. In one specific example, the tracking and processing subsystem may process and analyze such signals to determine an appropriate or preferred time to activate one or more cameras to take one or more still or moving images of the food. By leveraging sensors that track arm, hand, finger or wrist movement and/or the orientation and position of the camera to activate the camera and/or automate the image capture process, the complexity, capabilities and power consumption of the image-capture and image analysis system can be greatly reduced, and in certain cases better accuracy may be achieved. It also significantly reduces any privacy invasion concerns, as it now becomes possible to more precisely control the timing of image capturing and make it coincide with the cameras being focused on the food.

For example, the processor might analyze motion sensor inputs from an accelerometer, a gyroscope, a magnetometer, etc., to identify the optimal time to activate camera and capture picture and trigger the camera at that time, perhaps based on when the processor determines that the view region of the camera encompasses the food to be photographed. In one example, the processor determines the start of an eating event and signals the wearer to capture an image of the food being eaten and also determines the end of the eating event and again signals the wearer to capture an image of what remains of the food or the plate, etc. Such images can be processed to determine consumption amounts and/or to confirm consumption amounts already determined by the processor. In some embodiments, the image processing can be used as part of feedback to train machine learning that the processor uses.

In some embodiments, the system may use sensors that track the movement of the wearer's arm or hand and only activate the camera when the system determines from the movement sensing that the arm or hand are near the mouth. In another example, the system may activate the camera sometime between the start of the movement towards the mouth and the time when the arm or hand is the nearest to the mouth. In yet another example, the system may activate the camera sometime between the time when the arm or hand is the nearest to the mouth and the end of the movement away from the mouth.

As mentioned above, the position of the hand vis-à-vis the mouth can be determined by monitoring the pitch and a rising pitch indicating a start time of a movement towards the mouth and a falling pitch indicating an end time. Other definitions for nearest mouth position, start of movement and end of movement are also possible.

The position of the hand vis-à-vis the mouth can, for example, be determined by monitoring the pitch or the worn device and from there the pitch of the wearer's arm. The time corresponding to the peak of the pitch could be used as the moment in time when the hand is the nearest to the mouth. The time when the pitch starts rising could, for example, be used as the start time of the gesture. The time when the pitch stops falling could for example be used as the end time of the gesture.

The processing and analysis of sensor signals that track movement of a user's arm, hand or wrist may be combined with other methods such as the image capture of food as it enters the mouth as proposed to build in redundancy and improve the robustness of a dietary tracking and feedback system. For example, by processing and analysis of a user's arm, hand or wrist movement, information related to bite count and bite patterns would still be preserved, even if the camera were to be obscured or tampered with.

One or more of the sensor inputs may be still or streaming images obtained from one or more camera modules. Such images may require some level of processing and analysis. Processing and analysis methods may, among other methods, include one or more of the following methods: compression, deletion, resizing, filtering, image editing, and computer vision techniques to identify objects such as, for example, specific foods or dishes, or features such as, for example, portion sizes.

In addition to measuring bite counts and sip counts, the processor might analyze specifics, such as cadence and duration, to determine bite and sip sizes. Measuring the time that the wearer's hand, utensil or fluid container was near their mouth might be used to derive a "near-mouth" duration that is in turn used as an input to generate an estimate size of the bite or sip. The amount of rotation of the wrist when sipping might be useful for hydration tracking.

Measuring the amount of rotation of the wrist in one or more time segments that are within the start and the end of the gesture may also be used to estimate the size of the bite or sip. For example, a system may measure the amount of rotation of the wrist from a time sometime after the start of the gesture to the time when the arm or hand is the nearest to the mouth. The time corresponding to the peak of the pitch could be used as the moment in time when the hand is the nearest to the mouth. The time when the pitch starts rising could for example be used as the start time of the movement towards the mouth. The time when the pitch stops falling could for example be used as the end time of the movement away from the mouth. Other definitions for nearest mouth position, start of movement and end of movement are also possible. For example, the time when the roll changes direction could be used instead as the time when the arm or hand is the nearest to the mouth. The time when the roll stops changing in a certain direction or at a certain speed could be used as the start time of the movement towards the mouth. One or more still or streaming images may be analyzed and/or compared by the tracking and processing subsystem for one or multiple purposes including, but not limited to, the identification of food items, the identification of food content, the identification or derivation of nutritional information, the estimation of portion sizes and the inference of certain eating behaviors and eating patterns.

As one example, computer vision techniques, optionally combined with other image manipulation techniques may be used to identify food categories, specific food items and/or estimate portion sizes. Alternatively, images may be analyzed manually using a Mechanical Turk process or other crowdsourcing methods. Once the food categories and/or specific food items have been identified, this information can be used to retrieve nutritional information from one or more foods/nutrition databases.

As another example, information about a user's pace of eating or drinking may be inferred from analyzing and comparing multiple images captured at different times during the course of a food intake event. As yet another example, images, optionally combined with other sensor inputs, may be used to distinguish a sit-down meal from finger foods or snacks. As yet another example, the analysis of one image taken at the start of a food intake event and another image taken at the end of a food intake event may provide information on the amount of food that was actually consumed.

In a general case, sensor data is taken in by a processor that analyzes that sensor data, possibly along with prior recorded data and/or metadata about a person about whom the sensor data is sensing. The processor performs computations, such as those described herein, to derive a sequence of sensed gestures. A sensed gesture might be one of the gestures described elsewhere herein, along with pertinent data about the sensed gesture, such as the time of occurrence of the sensed gesture. The processor analyzes the sequence of sensed gestures to determine the start of a behavior event, such as the starting of an eating event.

The determination of the start of an eating event may be based on a sequence of sensed gestures, but it may also be based on the detection of a single event (possibly with non-gesture based context). For example, if the system detects a bite gesture with a reasonably high confidence level, the processor might consider that detection of that individual gesture to be the start of an eating event. The processor can also analyze the sequence of sensed gestures to determine the end of the behavior event. The determination of the end of an eating event may also be based on the absence of detected events. For example, if no bite gestures are detected in a given time period, the processor can assume that the eating event ended.

Knowing the start and end of a behavior event allows the processor to more accurately determine the gestures, since they are taken in context and/or the processor may enable additional sensors or place one or more sensors or other components in a higher performance state, such as in examples described elsewhere herein. Knowing the start and end of a behavior event also allows for power savings as, in some cases, it may be possible to place the worn device in a lower power mode outside certain behavior events. Also, aggregation of individual gestures into events, possibly combined with prior recorded data about similar behavior events from the same user or from other users in the past, allows the processor to derive meaningful characteristics about the behavior event. For example, an eating pace during breakfast, lunch, dinner can be determined in this manner. As another example, if the processor has a state for a current behavior and that current behavior is teeth brushing, gestures that might appear to be eating or drinking gestures would not be interpreted as eating or drinking gestures and thus not interpret sipping while teeth brushing as being consumption of liquids. Behavior events might be general events (eating, walking, brushing teeth, etc.) or more specific (eating with a spoon, eating with a fork, drinking from a glass, drinking from a can, etc.).

While it might be possible to decode an indirect gesture, such as detecting a pointing gesture and then determining the object that the sensed person is pointing at, of interest are gestures that themselves are directly part of the event being detected. Some gestures are incidental gestures, such as gestures associated with operating the device, in which case incidental gestures might be excluded from consideration.

In a specific example, the system uses some set of sensors to determine the start of an eating event with some confidence level and if the confidence level is higher than a threshold, the system activates additional sensors. Thus, the accelerometer sensor might be used to determine the start of an eating event with high confidence level, but a gyroscope is put in a low power mode to conserve battery life. The accelerometer alone can detect a gesture that is indicative of a probable bite or sip (e.g., an upward arm or hand movement or a hand or arm movement that is generally in the direction of the mouth), or a gesture that is generally indicative of the start of an eating event. Upon detection of a first gesture that is generally indicative of a possible start of an eating event, the additional sensors (e.g., gyroscope, etc.) may then be enabled. If a subsequent bite or sip gesture is detected, the processor determines that the start of an eating event had occurred and with a higher confidence level.

Knowing the start/end of a behavior event allows the processor to place one or more sensor or other components in a higher performance state for the duration of the behavior event. For example, when a start of a behavior event has been determined, the processor may increase the sampling rate of the accelerometer and/or gyroscope sensors used to detect gestures. As another example, when a start of a behavior event has been determined, the processor may increase the update rate at which sensor data are sent to electronic device 19 for further processing to reduce latency.

Referring again to FIG. 1, in addition to the tracking and processing subsystem, the system of FIG. 1 may also include a non-real-time analysis and learning subsystem 105. The non-real-time analysis and learning subsystem can perform an analysis on larger datasets that take a longer time to collect, such as historical data across multiple food intake events and/or data from a larger population. Methods used by the non-real-time analysis and learning subsystem may include, but are not limited to, data manipulation, algebraic computation, geo-tagging, statistical computing, machine learning and data analytics, computer vision, speech recognition, pattern recognition, compression and filtering.

Methods used by non-real-time analysis and learning subsystem 105 may, among other things, include data analytics on larger sets of data collected over longer periods of time. As an example, one or more data inputs may be captured over a longer period of time and across multiple food intake events to train a machine learning model. Such data inputs are hereafter referred to as training data sets. It is usually desirable that the period of time over which a training data set is collected, hereafter referred to as the training period, is sufficiently long such that the collected data is representative of a person's typical food intake.

A training data set may, among other things, include one or more of the following food intake related information: number of bites per food intake event, total bites count, duration of food intake event, pace of food intake or time between subsequent counts, categorization of food intake content such as for example distinguishing solid foods from liquids or sit-down meals from snacks or finger-foods. This information may be derived from one or more sensor inputs.

A training data set may furthermore include images of each or most items that were consumed during each of the food intake events within the training period. The images may be processed using computer vision and/or other methods to identify food categories, specific food items and estimate portion sizes. This information may then in turn be used to quantify the number of calories and/or the macro-nutrient content of the food items such as amounts of carbohydrates, fat, protein, etc.

In case the food was not consumed in its entirety, it may be desirable to take one picture of the food item at the start of the food intake event and one picture at the end of the food intake event to derive the portion of the food that was actually consumed. Other methods including, but not limited to, manual user input, may be used to add portion size information to the data in a training data set.

A training data set may furthermore include meta-data that do not directly quantify the food intake and/or eating behavior and patterns, but that may indirectly provide information, may correlate with food intake events and/or eating behavior and/or may be triggers for the occurrence of a food intake event or may influence eating habits, patterns and behavior. Such meta-data may, among other things, include one or more of the following: gender, age, weight, social-economic status, timing information about the food intake event such as date, time of day, day of week, information about location of food intake event, vital signs information, hydration level information, and other physical, mental or environmental conditions such as for example hunger, stress, sleep, fatigue level, addiction, illness, social pressure, and exercise.

One or more training data sets may be used to train one or more machine learning models which may then be used by one or more components of the dietary tracking and feedback systems to predict certain aspects of a food intake event and eating patterns and behaviors.

In one example, a model may be trained to predict the occurrence of a food intake event based on the tracking of one or more meta-data that may influence the occurrence of a food intake event. Other characteristics related to the probable food intake event, such as the type and/or amount of food that will likely be consumed, the pace at which a person will likely be eating, the duration of the food intake event, and/or the level of satisfaction a person will have from consuming the food may also be predicted. Meta-data may, among other things, include one or more of the following: gender, age, weight, social-economic status, timing information about the food intake event such as date, time of day, day of week, information about location of food intake event, vital signs information, hydration level information, and other physical, mental or environmental conditions such as for example hunger, stress, sleep, fatigue level, addiction, illness, social pressure, and exercise.

In another example, machine learning and data analytics may be applied to derive metrics that may be used outside the training period to estimate caloric or other macro-nutrient intake, even if only limited or no food intake sensor inputs or images are available. Meta-data may be used to further tailor the value of such metrics based on additional contextual information. Meta-data may, among other things, include one or more of the following: gender, age, weight, social-economic status, timing information about the food intake event such as date, time of day, day of week, information about location of food intake event, information about generic food category, vital signs information, hydration level information, calendar events information, phone call logs, email logs, and other physical, mental or environmental conditions such as for example hunger, stress, sleep, fatigue level, addiction, illness, social pressure, and exercise.

One example of such a metric would be "Calories per Bite". By combining the bites count with the caloric information obtained from image processing and analysis, a "Calories per bite" metric can be established from one or more training data sets. This metric can then be used outside the training period to estimate caloric intake based on bites count only, even if no images or only limited images are available.

Another metric could be "Typical Bite Size." By combining the bites count with the portion size information obtained from image processing and analysis, a "Typical Bite size" metric can be established from one or more training data sets. This metric can then be used outside the training period to estimate portion sizes based on bites count only, even if no images or only limited images are available. It may also be used to identify discrepancies between reported food intake and measured food intake based on bite count and typical bite size. A discrepancy may indicate that a user is not reporting all the food items that he or she is consuming. Or, alternatively, it may indicate that a user did not consume all the food that he or she reported.

Bite actions might be determined by a processor reading accelerometer and gyroscope sensors, or more generally by reading motion sensors that sense movement of body parts of the wearer. Then, by counting bites, a total number of bites can be inferred. Also, the time sequence of the bites can be used by the processor do deduce an eating pattern.

Non-real-time analysis and learning subsystem 105 may also be used track, analyze and help visualize larger sets of historical data, track progress against specific fixed or configured goals, and help establish such goals. It may furthermore be used to identify and track records, streaks and compare performance with that of friends or larger, optionally anonymous, populations.

Furthermore, in certain embodiments, non-real-time analysis and learning subsystem 105 may among other data manipulation and processing techniques, apply machine learning and data analytics techniques to predict the imminence of or the likelihood of developing certain health issues, diseases and other medical conditions. In this case, training typically requires historical food intake and/or eating behaviors data captured over longer periods of time and across a larger population. It is furthermore desirable that training data sets include additional meta-data such as age, weight, gender, geographical information, socio-economic status, vital signs, medical records information, calendar information, phone call logs, email logs and/or other information. Predictions may in turn be used to help steer health outcomes and/or prevent or delay the onset of certain diseases such as for example Diabetes.

Non-real-time and learning subsystem 105 may also be used to learn and extract more information about other aspects including, but not limited to, one or more of the following: a user's dietary and food preferences, a user's dining preferences, a user's restaurant preferences, and a user's food consumption. Such information may be used by the food intake tracking and feedback system to make specific recommendations to user. The food intake tracking and feedback system described in herein may also interface to or be integrated with other systems such as restaurant reservation systems online food or meal ordering systems, and others to facilitate, streamline or automate the process of food or meal ordering or reservations.

Non-real-time and learning subsystem 105 may also be used to monitor food intake over longer periods of times and detect any unusually long episodes of no food intake activity. Such episodes may, among other things, indicate that the user stopped using the device, intentional or unintentional tampering with the device, a functional defect of the device or a medical situation such as for example a fall or death or loss of consciousness of the user. Detection of unusually long episodes of no food intake activity may be used to send a notification or alert to the user, one or more of his caregivers, a monitoring system, an emergency response system, or to a third party who may have a direct or indirect interest in being informed about the occurrence of such episodes.

Another component of the system shown in FIG. 1 is the feedback subsystem 106. The feedback subsystem 106 provides one or more feedback signals to the user or to any other person to which such feedback information may be relevant. The feedback subsystem 106 may provide real-time or near real-time feedback related to a specific food intake event. Real-time or near real-time feedback generally refers to feedback given around the time of a food intake event. This may include feedback given during the food intake event, feedback given ahead of the start of a food intake event and feedback given sometime after the end of a food intake event. Alternatively, or additionally, the feedback subsystem may provide feedback to the user that is not directly linked to a specific food intake event.

Feedback methods used by the feedback subsystem may include, but are not limited to, haptic feedback whereby a haptic interface is used that applies forces, vibrations and/or motion to the user, audio feedback where a speaker or any other audio interfaces may be used, or visual feedback whereby a display, one or more LEDs and/or projected light patterns may be used. The feedback subsystem may use only one or a combination of more than one feedback method.

The feedback subsystem may be implemented in hardware, in software or in a combination of hardware and software. The feedback subsystem may be implemented on the same device as the food intake event detection subsystem 101 and/or the tracking and processing subsystem 103. Alternatively, the feedback subsystem may be implemented in a device that is separate from the food intake event detection subsystem 101 and/or the tracking and processing subsystem 103. The feedback subsystem may also be distributed across multiple devices, some of which may optionally house portions of some of the other subsystems illustrated in FIG. 1.

In one embodiment, the feedback subsystem may provide feedback to the user to signal the actual, probable or imminent start of a food intake event. The feedback subsystem may also provide feedback to the user during a food intake event to remind the user of the fact that a food intake event is taking place, to improve in-the-moment awareness and/or to encourage mindful eating. The feedback subsystem may also provide guidance on recommended portion sizes and/or food content, or provide alternative suggestions to eating. Alternative suggestions may be default suggestions or it may be custom suggestions that have been programmed or configured by the user at a different time.

Feedback signals may include, but are not limited to, periodic haptic feedback signals on a wearable device, sound alarms, display messages, or one or more notifications being pushed to his or her mobile phone display.

Upon receiving a signal that indicates the start of a food intake event, or sometime thereafter, the user may confirm that a food intake event is indeed taking place. Confirmation can be used to for example trigger logging of the event or may cause the system to prompt the user for additional information.

In another embodiment of the present disclosure, the feedback subsystem initiates feedback during a food intake event only if a certain threshold of one or more of the parameters being tracked is reached. As an example, if the time between subsequent bites or sips is being tracked, feedback to the user may be initiated if the time, possibly averaged over a multiple bites or sips, is shorter than a fixed or programmed value to encourage the user to slow down. Similarly, feedback may be initiated if a fixed or programmed bites or sips count is being exceeded.

In feedback subsystems where feedback is provided during a food intake event, the feedback provided by the feedback subsystem usually relates to specifics of that particular food intake event. However, other information including, but not limited to, information related to prior food intake events, biometric information, mental health information, activity or fitness level information, and environmental information may also be provided by the feedback subsystem.

In yet another embodiment of the present disclosure, the feedback subsystem may be sending one or more feedback signals outside a specific food intake event. In one example of such an embodiment, ambient temperature and/or other parameters that may influence hydration requirements or otherwise directly or indirectly measure hydration levels may be tracked. Such tracking may happen continuously or periodically, or otherwise independent from a specific food intake event. If one or more such parameters exceed a fixed or programmed threshold, a feedback signal may be sent to for example encourage him/her to take measures to improve hydration. The feedback subsystem might evaluate its inputs and determine that a preferred time for sending feedback is not during a food intake event, but after the food intake event has ended. Some of the inputs to the feedback subsystem might be from a food intake event, but some might be from other monitoring not directly measured as a result of the food intake event.

The decision to send a feedback signal may be independent of any food intake tracking, such as in the embodiment described in the previous paragraph. Alternatively, such a decision may be linked to food intake tracking across one or multiple food intake events. For example, in one embodiment of the current disclosure, the system described above could be modified to also track, either directly or indirectly, a person's intake of fluids. For different ambient temperature ranges, said embodiment could have pre-programmed fluid intake requirement thresholds. If for a measured ambient temperature, a person's intake of fluids, possibly tracked and accumulated over a certain period of time, is not meeting the threshold for said ambient temperature, the system may issue a feedback signal to advise said person to increase his or her levels of fluid intake.

Similarly, feedback signals or recommendations related to food intake may among other parameters, be linked to tracking of activity levels, sleep levels, social context or circumstances, health or disease diagnostics, and health or disease monitoring.

In yet another embodiment of the current disclosure, the feedback subsystem may initiate a feedback signal when it has detected that a food intake event has started or is imminent or likely. In such an embodiment, feedback could for example be used as a cue to remind the user log the food intake event or certain aspects of the food intake event that cannot be tracked automatically, or to influence or steer a person's food intake behavior and/or the amount or content of the food being consumed.

Information provided by the feedback subsystem may include but is not limited to information related to eating patterns or habits, information related to specific edible substances, such as for example the name, the description, the nutrient content, reviews, ratings and/or images of food items or dishes, information related to triggers for food intake, information related to triggers for eating patterns or habits, biometric or environmental information, or other information that may be relevant either directly or indirectly to a person's general food intake behavior, health and/or wellness.

The feedback subsystem may include the display of images of food items or dishes that have been consumed or may be consumed. Furthermore, the feedback subsystem may include additional information on said food items or dishes, such as for example indication of how healthy they are, nutrient content, backstories or preparation details, ratings, personalized feedback or other personalized information.

In certain embodiments of the current disclosure, the information provided by the feedback subsystem may include non-real-time information. The feedback subsystem may for example include feedback that is based on processing and analysis of historical data and/or the processing and analysis of data that has been accumulated over a larger population of users. The feedback subsystem may further provide feedback that is independent of the tracking of any specific parameters. As an example, the feedback subsystem may provide generic food, nutrition or health information or guidance.

In certain embodiments of the current disclosure, the user may interact with the feedback subsystem and provide inputs 116. For example, a user may suppress or customize certain or all feedback signals.

Non-real time feedback may, among other things, include historical data, overview of trends, personal records, streaks, performance against goals or performance compared to friends or other people or groups of people, notifications of alarming trends, feedback from friends, social networks and social media, caregivers, nutritionists, physicians etc., coaching advice and guidance.

Data or other information may be stored in data storage unit 104. It may be stored in raw format. Alternatively, it may be stored after it has been subject to some level of processing. Data may be stored temporarily or permanently. Data or other information may be stored for a wide variety of reasons including, but not limited to, temporary storage while waiting for processor or other system resources to become available, temporary storage to be combined with other data that may not be available until a later time, storage to be fed back to the user in raw or processed format through the feedback subsystem, storage for later consultation or review, storage for analysis for dietary and/or wellness coaching purposes, storage for statistical analysis across a larger population or on larger datasets, storage to perform pattern recognition methods or machine learning techniques on larger datasets.

The stored data and information, or portions thereof, may be accessible to the user of the system. It is also possible that the stored data and information or portions thereof, may be shared with or can be accessed by a third party. Third parties may include, but are not limited to, friends, family members, caregivers, healthcare providers, nutritionists, wellness coaches, other users, companies that develop and/or sell systems for dietary tracking and coaching, companies that develop and/or sell components or subsystems for systems for dietary tracking and coaching, and insurance companies. In certain circumstances, it may be desirable that data is made anonymous before making it available to a third party.

Figure 2:
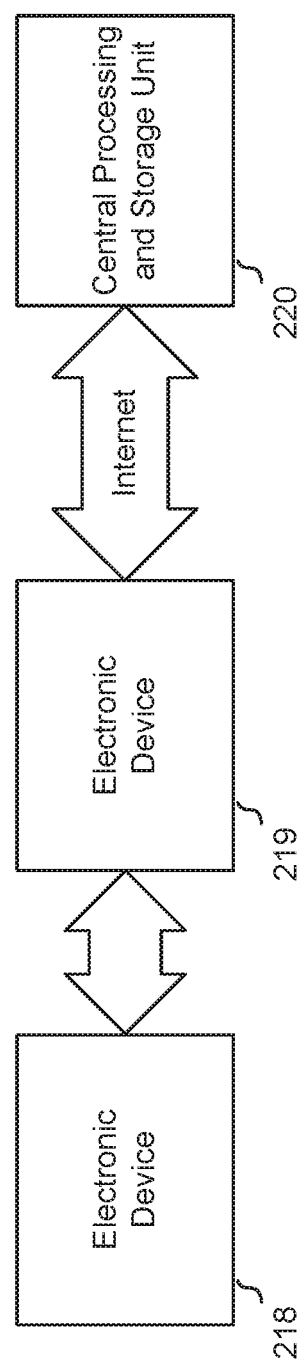
FIG. 2 is an illustrative example of a block diagram in which various embodiments can be implemented.

FIG. 2 illustrates some of the components disposed in an electronic system used for dietary tracking and coaching, in accordance with one embodiment of the present disclosure. The electronic system includes a first electronic device 218, a second electronic device 219 and a central processing and storage unit 220. A typical system might have a calibration functionality, to allow for sensor and processor calibration.

Variations of the system shown in FIG. 2 are also possible and are included in the scope of the present disclosure. For example, in one variation, electronic device 218 and electronic device 219 may be combined into a single electronic device. In another variation, the functionality of electronic device 218 may be distributed across multiple devices. In some variations, a portion of the functionality shown in FIG. 2 as being part of electronic device 218 may instead be included in electronic device 219. In some other variations, a portion of the functionality shown in FIG. 2 as being part of electronic device 219 may instead be included in electronic device 218 and/or central processing and storage unit 220. In yet another variation, the central processing and storage unit may not be present and all processing and storage may be done locally on electronic device 218 and/or electronic device 219. Other variations are also possible.

Figure 3:
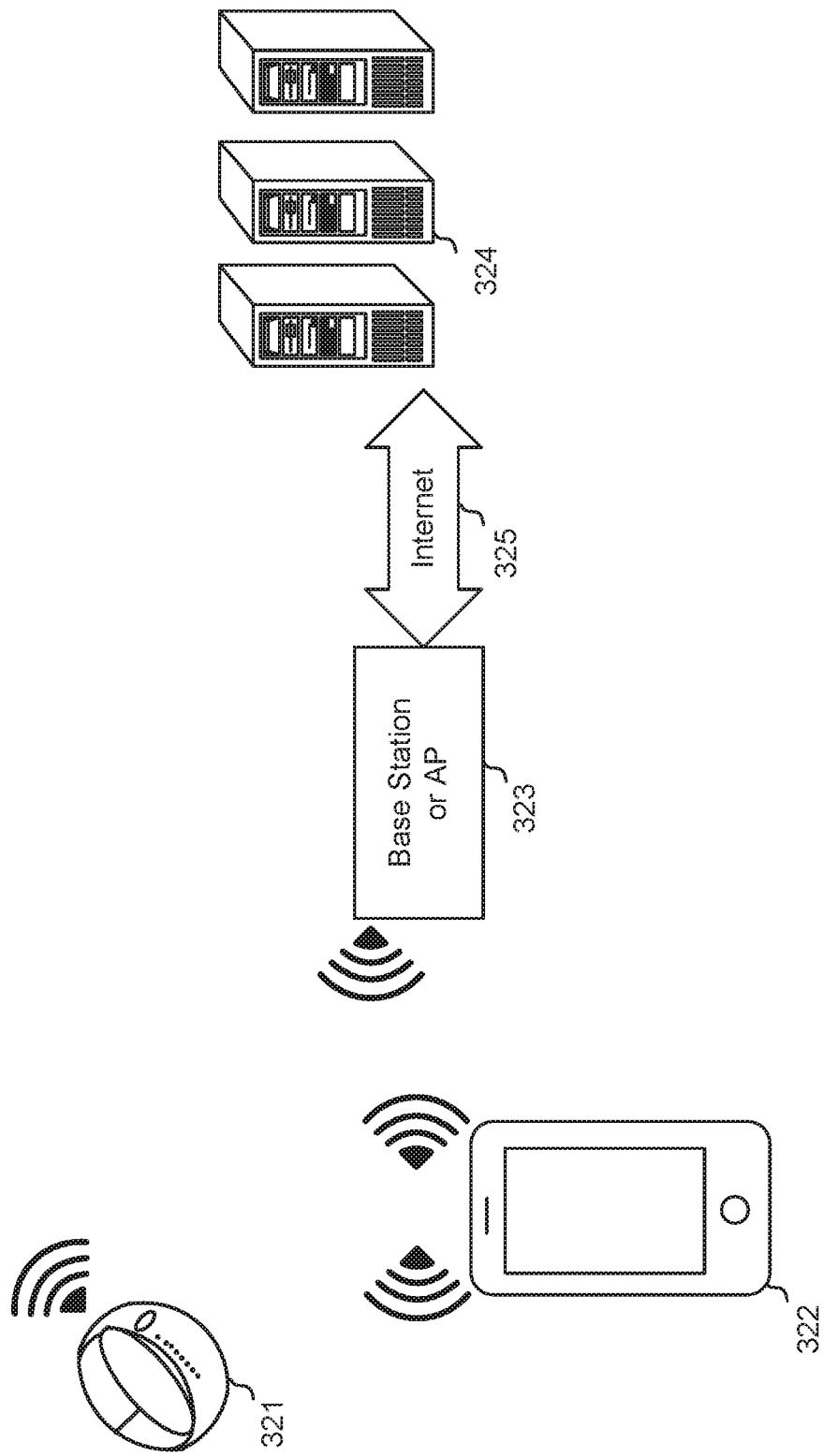
FIG. 3 is an illustrative example of an environment in accordance with at least one embodiment.

An example of the electronic system of FIG. 2 is shown in FIG. 3. Electronic device 218 may for example be a wearable device 321 that is worn around the wrist, arm or finger. Electronic device 218 may also be implemented as a wearable patch that may be attached to the body or may be embedded in clothing. Electronic device 218 may also be a module or add-on device that can for example be attached to another wearable device, to jewelry, or to clothing. Electronic device 219 may for example be a mobile device 322 such as a mobile phone, a tablet or a smart watch. Other embodiments of electronic device 219 and of electronic device 218 are also possible. The central processing and storage unit 220 usually comprises of one or more computer systems or servers and one or more storage systems. The central processing and storage unit 220 may for example be a remote datacenter 324 that is accessible via the Internet using an Internet connection 325. The central processing and storage unit 220 is often times shared among and/or accessed by multiple users.

The wearable device 321 may communicate with mobile device 322 over a wireless network. Wireless protocols used for communication over a wireless network between wearable device 321 and mobile device 322 may include, but is not limited to, Bluetooth, Bluetooth Smart (a.k.a. Bluetooth Low Energy), Bluetooth Mesh, ZigBee, Wi-Fi, Wi-Fi Direct, NFC, Cellular and Thread. A proprietary or wireless protocol, modifications of a standardized wireless protocol or other standardized wireless protocols may also be used. In another embodiment of the current disclosure, the wearable device 321 and the mobile device 322 may communicate over a wired network.

The mobile device 322 may communicate wirelessly with a base station or Access Point ("AP") 323 that is connected to the Internet via Internet connection 325. Via the Internet connection 325, mobile device 322 may transfer data and information from wearable device 321 to one or more central processing and storage unit 220 that reside at a remote location, such as for example a remote data center. Via Internet connection 325, mobile device 322 may also transfer data and information from one or more central processing and storage unit 220 that reside at a remote location to wearable device 321. Other examples are also possible. In some embodiments, the central processing and storage unit 220 may not be at a remote location, but may reside at the same location or close to the wearable device 321 and/or mobile device 322. Wireless protocols used for communication between the mobile device 322 and the base station or access point 323 may be the same as those between the mobile device and the wearable device. A proprietary or wireless protocol, modifications of a standardized wireless protocol or other standardized wireless protocols may also be used.

Figure 4:
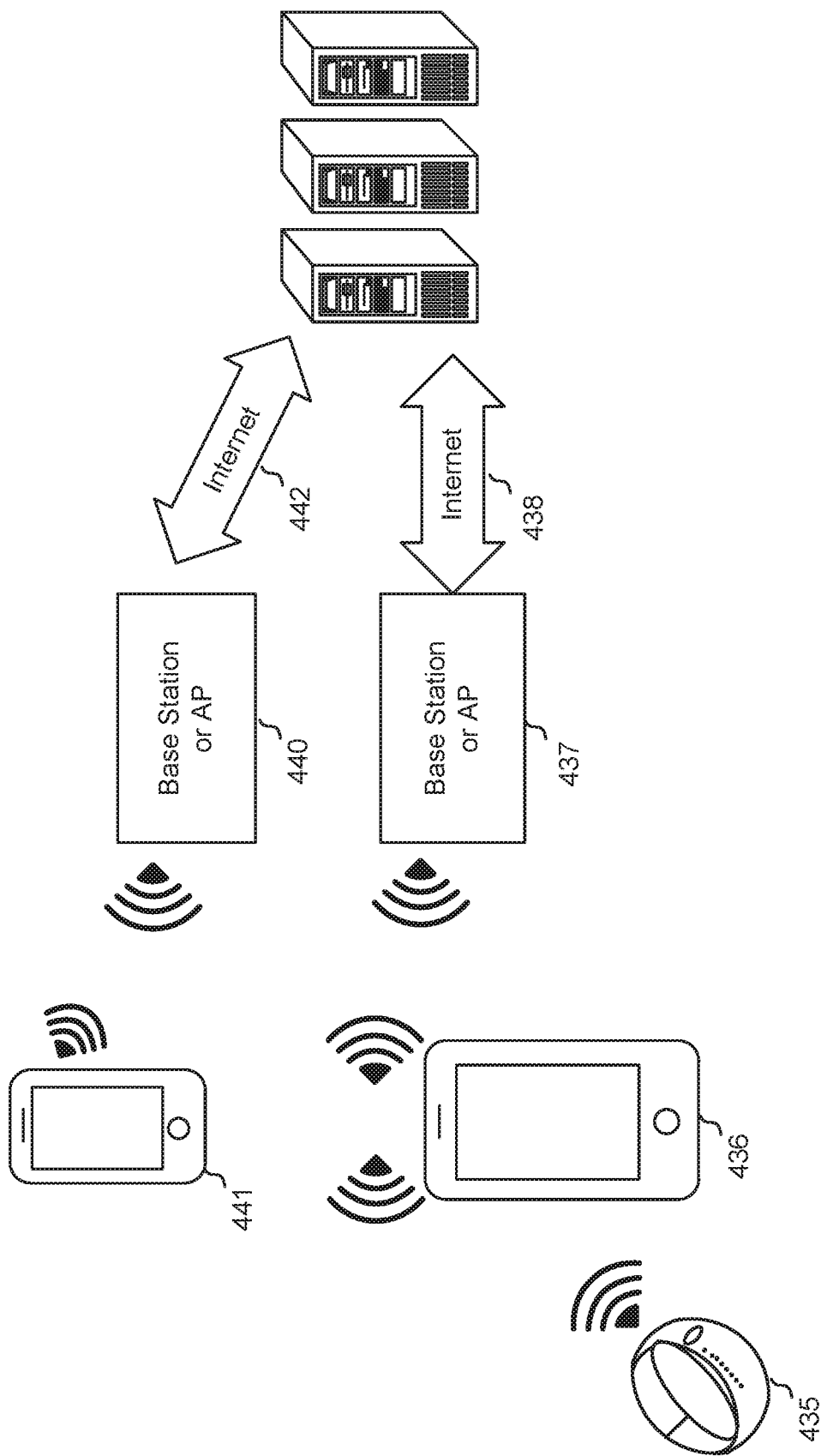
FIG. 4 is an illustrative example of an environment that includes communication with at least one additional device over the internet in accordance with at least one embodiment.

The electronic system of FIG. 2 may also send data, information, notifications and/or instructions to and/or receive data, information, notifications and/or instructions from additional devices that are connected to the Internet. Such devices could for example be a tablet, mobile phone, laptop or computer of one or more caregivers, members of the physician's office, coaches, family members, friends, people whom the user has connected with on social media, or other people to whom the user has given the authorization to share information. One example of such a system is shown in FIG. 4. In the example shown in FIG. 4, electronic device 441 is wirelessly connected to base station or Access Point 440 that is connected to the Internet via Internet connection 442. Examples of electronic device 441 may include, but are not limited to, a tablet, mobile phone, laptop, computer, or smart watch. Via Internet connection 442, electronic device 441 may receive data, instructions, notifications or other information from one or more central processing and storage units that may reside locally or at a remote location, such as for example a remote data center. The communication capability can include Internet connection 442 or other communication channels. Electronic device 441 may also send information, instructions or notifications to one or more computer servers or storage units 439. Central processing and storage unit 439 may forward this information, instructions or notifications to mobile device 436 via the Internet 438 and the base station or Access Point ("AP") 437.

Other examples are also possible. In some embodiments, the central processing and storage unit 439 may not be at a remote location, but may reside at the same location or close to the wearable device 435 and/or mobile device 436. FIG. 4 shows electronic device 441 as being wirelessly connected to the base station or Access Point. A wired connection between electronic device 441 and a router that connects to the Internet via an Internet connection 442 is also possible.

Figure 5:
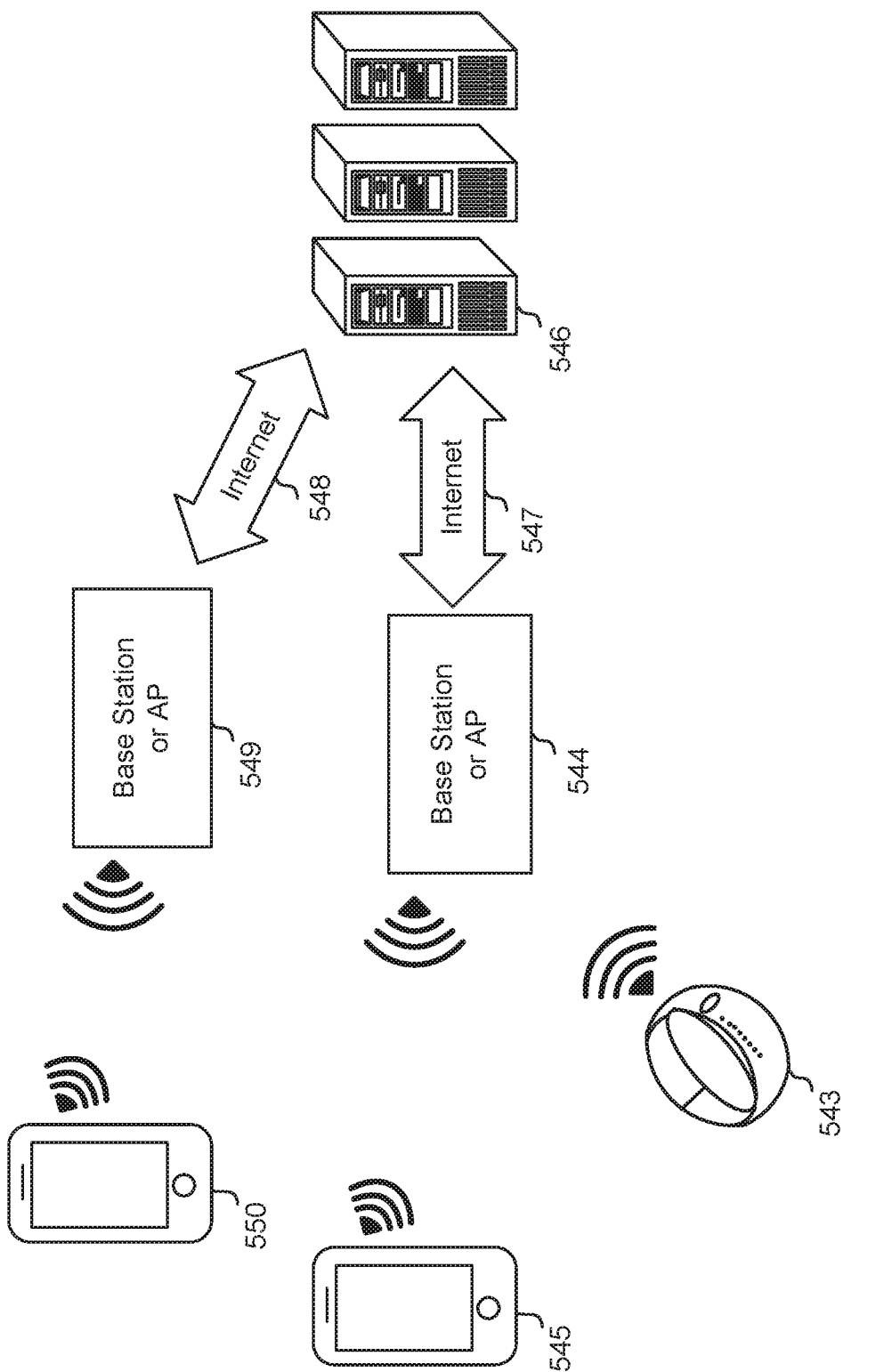
FIG. 5 is an illustrative example of an environment where a food intake monitoring and tracking device communicates directly with a base station or an access point in accordance with at least one embodiment.

FIG. 5 illustrates another embodiment of the present disclosure. In FIG. 5, a wearable device 543 can exchange data or other information directly with a central processing and storage system 546 via a base station or Access Point 544 and the Internet without having to go through mobile device 545. Mobile device 545 may exchange data or other information with wearable device 543 either via central processing and storage system 546 or via a local wireless or wired network. The central processing and storage system 546 may exchange information with one or more additional electronic devices 550.

Figure 6:
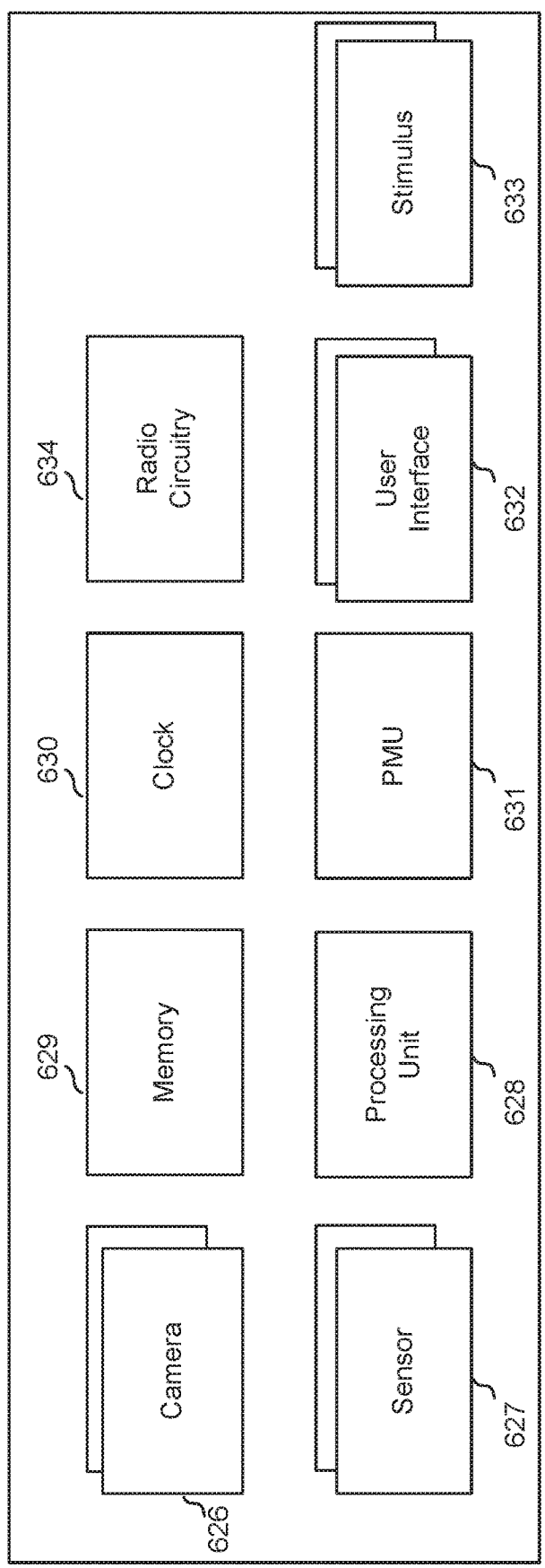
FIG. 6 is an illustrative example of a high-level block diagram of a monitoring and tracking device in accordance with at least one embodiment.

FIG. 6 illustrates some of the components disposed in electronic device 218, in accordance with one embodiment. Electronic device 218 typically includes, in part, one or more sensor units 627, a processing unit 628, memory 629, a clock or crystal 630, radio circuitry 634, and a power management unit ("PMU") 631. Electronic device 218 may also include one or more camera modules 626, one or more stimulus units 633 and one or more user interfaces 632. Although not shown, other components like capacitors, resistors, inductors may also be included in said electronic device 218. Power Management unit 631 may, among other things, include one or more of the following: battery, charging circuitry, regulators, hardware to disable the power to one or more components, power plug.

In many embodiments, electronic device 218 is a size constrained, power-sensitive battery operated device with a simple and limited user interface. Where power is limited, electronic device 218 might be programmed to save power outside of behavior events. For example, a processor in electronic device 218 might be programmed to determine the start of a behavior event, such as an eating event, and then power up additional sensors, place certain sensors in a higher performance mode and/or perform additional computations until the processor determines an end of the behavior event, at which point the processor might turn off the additional sensors, place certain sensors back in a lower performance mode and omit the additional computations.

For example, the processor might be programmed to disable all motion-detection related circuitry, with exception of an accelerometer. The processor could then monitor accelerometer sensor data and if those data indicate an actual or prominent food intake activity such as a bite or sip gesture, then the processor could activate additional circuitry, such as a data recording mechanism. The processor might use the accelerometer sensor data to monitor a pitch of the wearer's arm.

For example, the processor might measure pitch of the wearer's arm until the pitch exceeds a certain threshold, perhaps one indicative of a hand or arm movement towards the wearers' mouth. Once that is detected, the processor can change the state (such as by changing a memory location set aside for this state from "inactive" or "out-of-event" to "in an action" or "in-event") and activate additional circuitry or activate a higher performance mode of specific circuitry or components. In another embodiment, other accelerometer sensor data characteristics such as first integral of acceleration (velocity) or the second integral of acceleration (distance traveled), or characteristics related to or derived from the first and/or second integral of acceleration might be used, as determined from one or more accelerometer axis. A machine learning process might be used to detect specific movements and translate those to gestures.

An end of a food intake event might be detected by the processor by considering whether a certain time has expired since a last bite or sip movement or when other data (metadata about the wearer, motion-detection sensor data, and/or historical data of the wearer, or a combination of those). Based on those, the processor makes a determination that a food intake event is not likely and then changes the state of the electronic device to an inactive monitoring state, possibly a lower power mode.

The lower power mode might be implemented by the processor reducing the sampling rate of the accelerometer and/or gyroscope, powering down the gyroscope, reducing the update rate at which sensor data is transferred from the electronic device (such as electronic device 218) to the support device (such as electronic device 219), compressing the data before transferring the data from the sensing electronic device to the support electronic device.

In some embodiments of the present disclosure, some of the components that are shown in FIG. 5 as separate components may be combined. As an example, the processing unit, memory, radio circuitry and PMU functionality may entirely or in part be combined in a single wireless microcontroller unit ("MCU"). Other combinations are also possible. Similarly, components that are shown as a single component in FIG. 5 may be implemented as multiple components. As an example, the processing functionality may be distributed across multiple processors. Likewise, data storage functionality may be distributed across multiple memory components. Other examples of distributed implementations are also possible.

In another embodiment of the present disclosure, the radio circuitry may not be present and instead a different interface (such as for example a USB interface and cable) may be used to transfer data or information to and/or from the electronic device 218.

Stimulus unit 633 may provide feedback to the user of the electronic device. A stimulus unit 633 may include but is not limited to a haptic interface that applies forces, vibrations or motions to the user, a speaker or headphones interface that provides sounds to the user, and a display that provides visual feedback to the user.

In certain embodiments, the processing and analysis of signals from sensors embedded in electronic device 218 can detect when electronic device has been disabled, tampered with, removed from the body or is not being used. This can be used to conserve power, or to send a notification to the user, a friend or another person who might directly or indirectly have an interest in being notified if electronic device 218 is not being used properly.

Description Detection/Prediction of Start/End of Food Intake Event

In a preferred embodiment, the electronic device 218 is worn around the wrist, arm or finger and has one or more sensors that generate data necessary to detect the start and/or end of a food intake event. The electronic device 218 may also be integrated in a patch that can be attached to a person's arm or wrist. The electronic device 218 may also be a module or add-on device that can be attached to another device that is worn around the wrist, arm or finger. Sensors used to detect the start and/or end of a food intake event may among other sensors include one or more of the sensors described herein.

The raw sensor outputs may be stored locally in memory 629 and processed locally on processing unit 628 to detect if the start or end of a food intake event has occurred. Alternatively, one or more sensor outputs may be sent to electronic device 219 and/or the central processing and storage unit 220, either in raw or processed format, for further processing and to detect if the start or end of a food intake event has occurred. Regardless of where the processing for food intake detection occurs, sensor outputs in raw or processed format may be stored inside electronic device 218, inside electronic device 219 and/or inside the central processing and storage unit 220.

The sensor or sensors that generate data necessary for the detection of the start and/or end of a food intake event may be internal to electronic device 218. Alternatively, one or more of the sensors responsible for the detection of the start of a food intake event may be external to electronic device 218, but are able to relay relevant information to the electronic device 218 either directly through direct wireless or wired, communication with electronic device 218 or indirectly, through another device. It is also possible that electronic device 218 and the external sensor or sensors area able to relay information to electronic device 219, but are not able to relay information to one another directly.

In case of indirect communication through another device such as a mobile phone or other portable or stationary device, such third device is able to receive data or information from one or external sensor units, optionally processes such data or information, and forwards either the raw or processed data or information to electronic device 218. The communication to and from the electronic device 218 may be wired or wireless, or a combination of both.

Examples of sensors that may be external to electronic device 218 may be one or more sensors embedded in a necklace or pendant worn around the neck, one or more sensors embedded in patches that are attached to a different location on the body, one or more sensors embedded in a supplemental second wearable device that is worn around the other arm or wrist or on a finger of the other hand, or one or more sensors integrated in a tooth. In some embodiments, the electronic device is worn on one hand or arm but detects movement of the other hand or arm. In some embodiments, electronic devices are worn on each hand.

Information obtained from the non-real-time analysis and learning subsystem 105 may also be used, optionally in combination with information from one or more sensors 627, to predict or facilitate the detection of a probable, imminent or actual start/end of a food intake event.

It is often desirable that the detection and/or the prediction of the start and/or end of a food intake event happens autonomously without requiring user intervention. For example, if the actual, probable or imminent start of a food intake event is predicted or detected autonomously, this information can be used as a trigger to activate or power up specific components or circuits that are only needed during a food intake event. This can help conserve power and extend the battery life of electronic device 218. The prediction or detection of an actual, probable or imminent start of a food intake event can also be used to issue a cue or reminder to the user. A cue can for example be sent to the user to remind him/her to take further actions including, but not limited to, logging the food intake event or taking a picture of the food. Upon detection of the start of a food intake event, one or more cues, possibly spread out over the duration of the food intake event, to remind the user that a food intake event is taking place and improving in-the-moment awareness and/or encourage mindful eating. Cues or reminders may for example be sent through discrete haptic feedback using one or more stimulus units 633. Other methods using one or more user interfaces 632, such as for example one or more LEDs, a display message, or an audio signal, are also possible. Alternatively, mobile device 219 may be used to communicate cues, reminders or other information such as for example portion size recommendations or alternative suggestions to eating to the user.

If the actual, probable or imminent end of a food intake event is predicted or detected autonomously, this information can be used as a trigger to power down or at least put in a lower power mode one or more circuits or components of electronic device 218 that are only needed during a food intake event. This can help conserve power and extend the battery life of electronic device 218. The detection of the actual, probable or imminent end of a food intake event may also be used to modify or suspend the feedback provided to the user by one or more stimulus units 633, by one or more of the user interfaces 632, and/or by mobile device 219.

In some embodiments of the present disclosure, the detection or prediction of the actual, probable or imminent start and/or end of a food intake event may not be entirely autonomously. For example, the user may be required to make a specific arm, wrist, hand or finger gesture to signal to electronic device 218 the actual, probable or imminent start and/or end of a food intake event. The arm, wrist, hand or finger gesture is then detected by one or more sensors inside electronic device 218. It is usually desirable that the arm, wrist, hand or finger gesture or gestures required to indicate the start and/or end of a food intake event can be performed in a subtle and discrete way. Other methods may also be used. For example, the user may be asked to push a button on electronic device 218 to indicate the start and/or end of a food intake event. Voice activation commands using a microphone that is built into electronic device 18 may also be used. Other methods are also possible.

Description of Tracking of Eating Behaviors and Patterns

In a particular embodiment, the electronic device 218 is worn around the wrist, arm or finger and has one or more sensors that generate data that facilitate the measurement and analysis of eating behaviors, patterns and habits. Sensors used for measuring and analyzing certain eating behaviors and patterns may include one or more of the sensors described herein.

Relevant metrics that may be used to quantify and track eating behaviors and eating patterns may include, but are not limited to, the time between subsequent bites or sips, the distance between the plate and the user's mouth, the speed of arm movement towards and/or away from the user's mouth, and the number of bites or sips during a single food intake event, derived from the total count of arm movements corresponding to a bite or sip, specific chewing behavior and characteristics, the time between taking a bite and swallowing, amount of chewing prior to swallowing.

The raw sensor outputs may be stored locally in memory 29 and processed locally on processing unit 28. Alternatively, one or more sensor outputs may be sent to electronic device 19 and/or the central processing and storage unit 20, either in raw or in processed format, for further processing and analysis. Regardless of where the processing and analysis of eating behaviors and patterns occurs, sensor outputs in raw or processed format may be stored inside electronic device 18, inside electronic device 19 and/or inside the central processing and storage unit 20.

In some embodiments, the generation, collection and/or processing of data that facilitate the measurement and analysis of eating behaviors, patterns and habits may be continuously, periodically or otherwise independently of the start and/or end of a food intake event. Alternatively, the generation, collection and/or processing of data that facilitate the measurement and analysis of eating behavior and patterns may occur only during a food intake event or be otherwise linked to a specific food intake event. It is also possible that some sensor data are being generated, collected and/or processed continuously, periodically or otherwise independently of the start and/or end of a food intake event whereas other sensor data are taken during a food intake event or otherwise linked to a food intake event.

The sensor or sensors that generate data necessary for measuring and analyzing eating behaviors and eating patterns may be internal to electronic device 18. Alternatively, one or more of the that generate data necessary for measuring and analyzing eating behaviors and eating patterns may be external to electronic device 18, but are able to relay relevant information to electronic device 18 either directly through direct wireless or wired, communication with electronic device 18 or indirectly, through another device.

In case of indirect communication through another device such as a mobile phone or other portable or stationary device, such third device is able to receive data or information from the external sensor unit, optionally processes such data or information, and forwards either the raw or processed data or information to the tracking device. The communication to and from the electronic device 18 may be wired or wireless, or a combination of both.

Examples of sensors that may be external to electronic device 18 may be one or more sensors embedded in a necklace or pendant worn around the neck, one or more sensors embedded in patches that are attached to a different location on the body, one or more sensors embedded in a supplemental second wearable device that is worn around the other arm or wrist or on a finger of the other hand, or one or more sensors integrated in a tooth.

Description of Use of Camera Module and Image Capture

While use of a camera to capture images of food have been proposed in the prior art, they typically rely on the user taking pictures with his or her mobile phone or tablet. Unfortunately, image capture using a mobile phone or tablet imposes significant friction of use, may not be socially acceptable in certain dining situations or may interfere with the authenticity of the dining experience. It is often times not desirable or inappropriate that the user needs to pull out his or her mobile phone, unlock the screen, open a Mobile App and take a picture using the camera that is built into the mobile phone.

If user intervention is required, it is generally desirable that the user intervention can be performed in a subtle and discrete manner and with as little friction as possible. In order to minimize the friction of use, it is often times desirable that the image capture can be initiated from electronic device 18 directly.

While the examples provided herein use image capture of food and meal scenarios as examples, upon reading this disclosure, it should be clear that the methods and apparatus described herein can be applied to image capture of objects and scenes other than foods and meal scenarios. For example, a viewfinder-less camera can have application outside of the food event capture domain.

In some embodiments, electronic device 18 is worn around the wrist, arm or finger and includes one or more camera modules 26. One or more camera modules 26 may be used for the capture of still images in accordance with one embodiment of the present disclosure, and for the capture of one or more video streams in accordance with another embodiment of the present disclosure. In yet another embodiment of the present disclosure, a combination of still and streaming images is also possible.

One or more camera modules may also be included in a device that is worn at a different location around the body, such as a necklace or pendant that is worn around the neck, or a device that is attached to or integrated with the user's clothing, with the camera or camera modules preferably aiming towards the front so that it can be in line of sight with the food being consumed.

In some embodiments, activation of a camera module and/or image capture by a camera module may require some level of user intervention. User intervention may, among other things, include pressing a button, issuing a voice command into a microphone that is built into electronic device 18 or mobile device 19, making a selection using a display integrated in electronic device 18 or mobile device 19, issuing a specific arm, wrist, hand or finger gesture, directing the camera so that the object of interest is within view of the camera, removing obstacles that may be in the line of sight between the camera and the object of interest, and/or adjusting the position of the object of interest so that it is within view of the camera. Other user intervention methods, or a combination of multiple user intervention methods are also possible.

In one embodiment of the present disclosure, a camera module is built into an electronic device, such as a wearable device, that may not have a viewfinder, or may not have a display that can give feedback to the user about the area that is within view of the camera. In this case, the electronic device may include a light source that projects a pattern of visible light onto a surface or onto an object to indicate to the user the area that is within the view of the camera. One or more Light Emitting Diodes (LEDs) may be used as the light source. Other light sources including, but not limited to, laser, halogen or incandescent light sources are also possible. The pattern of visible light may, among other things, be used by the user to adjust the position of the camera, adjust the position the object of interest and/or remove any objects that are obstructing the line of sight between the object of interest and the camera.

The light source may also be used to communicate other information to the user. As an example, the electronic device may use inputs from one or more proximity sensors, process those inputs to determine if the camera is within the proper distance range from the object of interest, and use one or more light sources to communicate to the user that the camera is within the proper distance range, that the user needs to increase the distance between camera and the object of interest, or that the user needs to reduce the distance between the camera and the object of interest.

The light source may also be used in combination with an ambient light sensor to communicate to the user if the ambient light is insufficient or too strong for an adequate quality image capture.

The light source may also be used to communicate information including, but not limited, to a low battery situation or a functional defect.

The light source may also be used to communicate dietary coaching information. As an example, the light source might, among other things, indicate if not enough or too much time has expired since the previous food intake event, or may communicate to the user how he/she is doing against specific dietary goals.

Signaling mechanisms to convey specific messages using one or more light sources may include, but are not limited to, one or more of the following: specific light intensities or light intensity patterns, specific light colors or light color patterns, specific spatial or temporal light patterns. Multiple mechanisms may also be combined to signal one specific message.

In another embodiment of the current disclosure, a camera module may be built into an electronic device 18, such as a wearable device, that does not have a viewfinder or does not have a display that can give feedback to the user about the area that is within view of the camera. Instead of or in addition to using a light source, one or more images captured by the camera module, possibly combined with inputs from other sensors that are embedded in electronic device 18 may be sent to the processing unit inside electronic device 18, the processing unit inside electronic device 19, and/or the central processing and storage unit 20 for analysis and to determine if the object of interest is within proper view and/or proper focal range of the camera. The results of the analysis may be communicated to the user using one of the feedback mechanisms available in electronic device 18 including, but not limited to, haptic feedback, visual feedback using one or more LEDs or a display, and/or audio feedback.

In some other embodiments of the present disclosure, electronic device 18 may capture one or more images without any user intervention. Electronic device 18 may continuously, periodically or otherwise independently of any food intake event capture still or streaming images. Alternatively, electronic device 18 may only activate one or more of its camera modules around or during the time of a food intake event. As an example, an electronic device may only activate one or more of its camera modules and capture one or more images after the start of a food intake event has been detected and before the end of a food intake event has been detected. It may use one or more of its camera modules to capture one of more images of food items or dishes in their entirety, or of a portion of one or more food items or dishes.

In some embodiments, one camera may be used to capture one or more images of food items that are on a plate, table or other stationary surface, and a second camera may be used to capture one or more images of food items that are being held by the user, such as for example finger foods or drinks. The use of more than one camera may be desirable in situations where no user intervention is desirable and the position, area of view or focal range of a single camera is not suite to capture all possible meal scenarios.

In one example embodiment, the position, the orientation and the angle of view of the camera are such that an image or video capture is possible without any user intervention. In such an embodiment, the wearable device may use a variety of techniques to determine the proper timing of the image or video stream capture such that it can capture the food or a portion of the food being consumed. It may also choose to capture multiple images or video streams for this purpose. Techniques to determine the proper timing may include, but are not limited to, the following: sensing of proximity, sensing of acceleration or motion (or absence thereof), location information. Such sensor information may be used by itself or in combination with pattern recognition or data analytics techniques (or a combination of both) to predict the best timing for the image or video capture. Techniques may include, but are not limited to, training of a model based on machine learning.

The captured still and/or streaming images usually require some level of processing. Processing may include but is not limited to compression, deletion, resizing, filtering, image editing, and computer vision techniques to identify objects such as for example specific foods or dishes, or features such as for example portion sizes. Processing units that may be used to process still or streaming images from the camera module or modules, regardless of whether or not the camera module or modules are internal to the electronic device 18, include, but are not limited to, the processing unit inside the electronic device 18, the processing unit inside electronic device 19 and/or a central processing and storage unit 20 which may reside at the same location as where the electronic device is being used or alternatively, may reside at a remote location (e.g., in a cloud server) in which case it may be accessed via the internet. The image processing may also be distributed among a combination of the abovementioned processing units.

Examples of local processing may include but are not limited to: selection of one or more still images out of multiple images or one or more video streams, compression of images or video stream, application of computer vision algorithms on one or more images or video streams.

Local processing may include compression. In case of compression, a compressed image may be transmitted as part of a time critical transaction whereas its non-compressed version may be saved for transmission at a later time.

One or more still or streaming images may be analyzed and/or compared for one or multiple purposes including, but not limited to, the detection of the start and/or end of a food intake event, the identification of food items, the identification of food content, the identification or derivation of nutritional information, the estimation of portion sizes and the inference of certain eating behaviors and eating patterns.

As one example, computer vision techniques, optionally combined with other image manipulation techniques may be used to identify food categories, specific food items and/or estimate portion sizes. Alternatively, images may be analyzed manually using a Mechanical Turk process or other crowdsourcing methods. Once the food categories and/or specific food items have been identified, this information can be used to retrieve nutritional information from one or more foods/nutrition databases.

As another example, information about a user's pace of eating or drinking may be inferred from analyzing and comparing multiple images captured at different times during the course of a food intake event. As yet another example, images, optionally combined with other sensor information, may be used to distinguish a sit-down meal from finger foods or snacks. As yet another example, the analysis of one image taken at the start of a food intake event and another image taken at the end of a food intake event may provide information on the amount of food that was actually consumed.

Description of User Feedback

In a preferred embodiment of the present disclosure, the electronic device 18 is worn around the wrist, arm or finger and has one or more stimulus units and/or user interfaces that allow for feedback to the user or the wearer of the electronic device. In a different embodiment of the present disclosure, electronic device 18 may be implemented as a wearable patch that may be attached to the body or may be embedded in clothing.

Feedback usually includes feedback that is food or food intake related. Feedback methods may include, but are not limited to, haptic feedback, visual feedback using LEDs or a display or audio feedback. In one such embodiment, electronic device 18 may have a haptic interface that vibrates once or multiple times when the start and/or end of a food intake event have been detected. In another embodiment, electronic device 18 may have a haptic interface that vibrates once or multiple times when the tracking and processing subsystem identifies that the wearer of the device is consuming food and is showing eating behavior that is exceeding certain programmed thresholds, such as for example eating too fast, too slow or too much. Alternatively, the haptic interface may vibrate one or more times during a food intake event, independent of any specific eating behavior, for example to remind the wearer of the fact that a food intake event is taking place and/or to improve in-the-moment awareness and to encourage mindful eating. Other feedback methods are also possible, and different metrics or criteria may be used to trigger an activation of such feedback methods.

In a different embodiment of the present disclosure, feedback is provided to the user through a device that is separate from the electronic device 18. One or more stimulus units and/or user interfaces required to provide feedback to the user may be external to electronic device 18. As an example, one or more stimulus units and/or user interfaces may be inside electronic device 19, and one or more of said stimulus units and/or user interfaces inside electronic device 19 may be used to provide feedback instead of or in addition to feedback provided by electronic device 18. Examples may include, but are not limited to, messages being shown on the display of electronic device 19, or sound alarms being issued by the audio subsystem embedded inside electronic device 19.

Alternatively, feedback may be provided through a device that is separate from both electronic device 18 and electronic device 19, but that is able to at a minimum, either directly or indirectly, receive data from at least one of those devices.

In addition to or instead of feedback provided around or during the time of a food intake event, the system of FIG. 2 or FIG. 3 may also provide feedback that may span multiple food intake events or may not linked to a specific food intake event or set of food intake events. Examples of such feedback may include, but are not limited to, food content and nutritional information, historical data summaries, overviews of one or more tracked parameters over an extended period of time, progress of one or more tracked parameters, personalized dietary coaching and advice, benchmarking of one or more tracked parameters against peers or other users with similar profile.

Detailed Description of Specific Embodiments

In one specific embodiment of the present disclosure, electronic device 218 is a wearable device in the form factor of a bracelet or wristband that is worn around the wrist or arm of a user's dominant hand. Electronic device 219 is a mobile phone and central processing and storage unit 220 is one or more compute servers and data storage that are located at a remote location.

Figure 7:
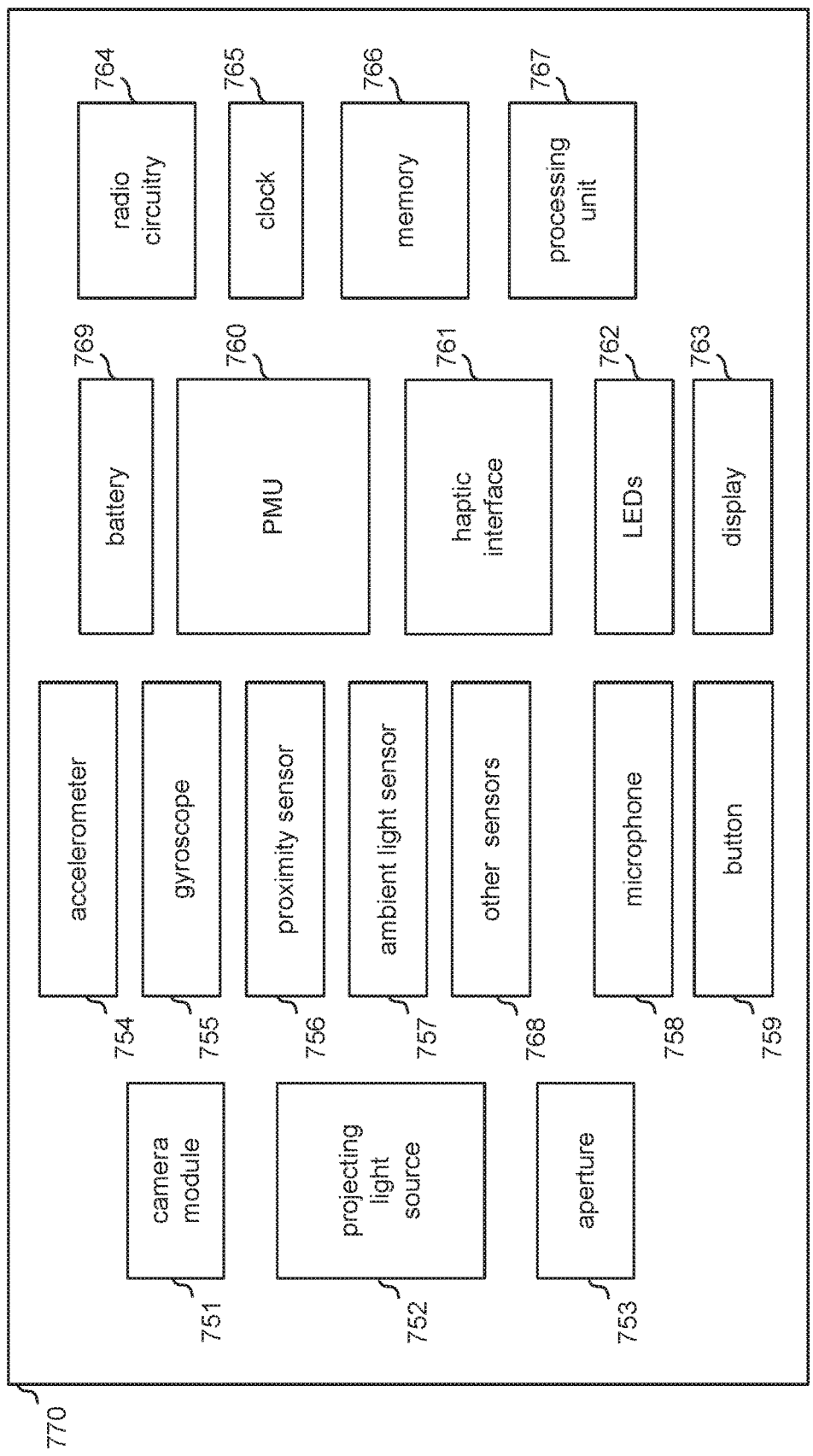
FIG. 7 is an illustrative example of a block diagram of a monitoring and tracking device in accordance with at least one embodiment.

One possible implementation of a wearable bracelet or wristband in accordance with aspects of the present invention is shown in FIG. 7. Wearable device 770 may optionally be implemented using a modular design, wherein individual modules include one or more subsets of the components and overall functionality. The user may choose to add specific modules based on his personal preferences and requirements.

The wearable device 770 may include a processor, a program code memory and program code (software) stored therein and/or inside electronic device 219 to optionally allow users to customize a subset of the functionality of wearable device 770.

Wearable device 770 relies on battery 769 and Power Management Unit ("PMU") 760 to deliver power at the proper supply voltage levels to all electronic circuits and components. Power Management Unit 760 may also include battery-recharging circuitry. Power Management Unit 760 may also include hardware such as switches that allows power to specific electronics circuits and components to be cut off when not in use.

When there is no behavior event in progress, most circuitry and components in wearable device 770 are switched off to conserve power. Only circuitry and components that are required to detect or help predict the start of a behavior event may remain enabled. For example, if no motion is being detected, all sensor circuits but the accelerometer may be switched off and the accelerometer may be put in a low-power wake-on-motion mode or in another lower power mode that consumes less power than its high performance active mode. The processing unit may also be placed into a low-power mode to conserve power. When motion or a certain motion pattern is detected, the accelerometer and/or processing unit may switch into a higher power mode and additional sensors such as for example the gyroscope and/or proximity sensor may also be enabled. When a potential start of an event is detected, memory variables for storing event-specific parameters, such as gesture types, gesture duration, etc. can be initialized.

In another example, upon detection of motion, the accelerometer switches into a higher power mode, but other sensors remain switched off until the data from the accelerometer indicates that the start of a behavior event has likely occurred. At that point in time, additional sensors such as the gyroscope and the proximity sensor may be enabled.

In another example, when there is no behavior event in progress, both the accelerometer and gyroscope are enabled but at least one of either the accelerometer or gyroscope is placed in a lower power mode compared to their regular power mode. For example, the sampling rate may be reduced to conserve power. Similarly, the circuitry required to transfer data from electronic device 218 to electronic device 219 may be placed in a lower power mode. For example, radio circuitry 764 could be disabled completely. Similarly, the circuitry required to transfer the data from electronic device 218 to electronic device 219 may be placed in a lower power mode. For example, it could be disabled completely until a possible or likely start of a behavior event has been determined. Alternatively, it may remain enabled but in a low power state to maintain the connection between electronic device 218 and electronic device 219 but without transferring sensor data.

In yet another example, all motion-detection related circuitry, including the accelerometer may be switched off, if based on certain meta-data it is determined that the occurrence of a particular behavior event such as a food intake event is unlikely. This may for example be desirable to further conserve power. Meta-data used to make this determination may, among other things, include one or more of the following: time of the day, location, ambient light levels, proximity sensing, and detection that wearable device 770 has been removed from the wrist or hand, detection that wearable device 770 is being charged. Meta-data may be generated and collected inside wearable device 770. Alternatively, meta-data may be collected inside the mobile phone or inside another device that is external to wearable device 770 and to the mobile phone and that can either directly or indirectly exchange information with the mobile phone and/or wearable device 770. It is also possible that some of the meta-data are generated and collected inside wearable device 770 whereas other meta-data are generated and collected in a device that is external to wearable device 770. In case some or all of the meta-data are generated and collected external to wearable device 770, wearable device 770 may periodically or from time to time power up its radio circuitry 764 to retrieve meta-data related information from the mobile phone or other external device.

In yet another embodiment of the invention, some or all of the sensors may be turned on or placed in a higher power mode if certain meta-data indicates that the occurrence of a particular behavior event, like for example a food intake event is likely. Meta-data used to make this determination may, among other things, include one or more of the following: time of the day, location, ambient light levels and proximity sensing. Some or all of the meta-data may be collected inside the mobile phone or inside another device that is external to wearable device 770 and to the mobile phone and that can either directly or indirectly exchange information with the mobile phone and/or wearable device 770. In case some or all of the meta-data are generated and collected external to wearable device 770, wearable device 770 may periodically or from time to time power up its radio circuitry 764 to retrieve meta-data related information from the mobile phone or other external device.

The detection of the start of a behavior event, such as for example a food intake event may be signaled to the user via one of the available user interfaces on wearable device 770 or on the mobile phone to which wearable device 770 is connected. As one example, haptic interface 761 inside wearable device 770 may be used for this purpose. Other signaling methods are also possible.

The detection of the start of a behavior event such as for example a food intake event may trigger some or all of the sensors to be placed or remain in a high-power mode or active mode to track certain aspects of a user's eating behavior for a portion or for the entirety of the food intake event. One or more sensors may be powered down or placed in a lower power mode when or sometime after the actual or probable end of the behavior event (the deemed end of the behavior event) has been detected. Alternatively, it is also possible that one or more sensors are powered down or placed in a lower power mode after a fixed or programmable period of time.

Sensor data used to track certain aspects of a user's behavior, such as for example a user's eating behavior, may be stored locally inside memory 766 of wearable device 770 and processed locally using processing unit 767 inside wearable device 770. Sensor data may also be transferred to the mobile phone or remote compute server, using radio circuitry 764, for further processing and analysis. It is also possible that some of the processing and analysis is done locally inside wearable device 770 and other processing and analysis is done on the mobile phone or on a remote compute server.

The detection of the start of a behavior event, such as for example the start of a food intake event, may trigger the power up and/or activation of additional sensors and circuitry such as for example the camera module 751. Power up and/or activation of additional sensors and circuitry may happen at the same time as the detection of the start of a food intake event or sometime later. Specific sensors and circuitry may be turned on only at specific times during a food intake event when needed and may be switched off otherwise to conserve power.

It is also possible that the camera module only gets powered up or activated upon explicit user intervention such as for example pushing and holding a button 759. Releasing the button may turn off the camera module again to conserve power.

When the camera module 751 is powered up, projecting light source 752 may also be enabled to provide visual feedback to the user about the area that is within view of the camera. Alternatively, projecting light source 752 may only be activated sometime after the camera module has been activated. In certain cases, additional conditions may need to be met before projecting light source 752 gets activated. Such conditions may, among other things, include the determination that projecting light source 752 is likely aiming in the direction of the object of interest, or the determination that wearable device 752 is not moving excessively.

In one specific implementation, partially depressing button 759 on wearable device 770 may power up the camera module 751 and projecting light source 752. Further depressing button 759 may trigger camera module 751 to take one or more still images or one or more streaming images. In certain cases, further depressing button 759 may trigger a de-activation, a modified brightness, a modified color, or a modified pattern of projected light source 752 either before or coinciding with the image capture. Release of button 759 may trigger a de-activation and/or power down of projected light source 752 and/or of camera module 751.

Images may be tagged with additional information or meta-data such as for example camera focal information, proximity information from proximity sensor 756, ambient light levels information from ambient light sensor 757, timing information etc. Such additional information or meta-data may be used during the processing and analysis of food intake data.

Various light patterns are possible and may be formed in various ways. For example, it may include a mirror or mechanism to reflect projecting light source 752 such that projected light source 752 produces one or more lines of light, outlines the center or boundaries a specific area, such as a cross, L-shape, circle, rectangle, multiple dots or lines framing the field of view or otherwise giving to the user visual feedback about the field of view.

One or more Light Emitting Diodes (LEDs) may be used as project light source 752. The pattern of visible light may, among other things, be used by the user to adjust the position of the camera, adjust the position the object of interest and/or remove any objects that are obstructing the line of sight between the object of interest and the camera.

Projected light source 752 may also be used to communicate other information to the user. As an example, the electronic device me use inputs from one or more proximity sensors, process those inputs to determine if the camera is within the proper distance range from the object of interest, and use one or more light sources to communicate to the user that the camera is within the proper distance range, that the user needs to increase the distance between camera and the object of interest, or that the user needs to reduce the distance between the camera and the object of interest.

The light source may also be used in combination with an ambient light sensor to communicate to the user if the ambient light is insufficient or too strong for an adequate quality image capture.

The light source may also be used to communicate information including, but not limited to, a low battery situation or a functional defect.

The light source may also be used to communicate dietary coaching information. As an example, the light source might, among other things, indicate if not enough or too much time has expired since the previous food intake event, or may communicate to the user how he/she is doing against specific dietary goals.

Signaling mechanisms to convey specific messages using one or more projecting light sources may include, but are not limited to, one or more of the following: specific light intensities or light intensity patterns, specific light colors or light color patterns, specific spatial or temporal light patterns. Multiple mechanisms may also be combined to signal one specific message.

Microphone 758 may be used by the user to add specific or custom labels or messages to a food intake event and/or image. Audio snippets may be processed by a voice recognition engine.

In certain embodiments, the accelerometer possibly combined with other sensors may, in addition to tracking at least one parameter that is directly related to food intake and/or eating behavior, also be used to track one or more parameters that are not directly related to food intake. Such parameters may, among other things, include activity, sleep or stress.

Specific Embodiments Without Built-In Camera

In a different embodiment, electronic device 218 may not have any built-in any image capture capabilities. Electronic device 218 may be a wearable device such as a bracelet or wristband worn around the arm or wrist, or a ring worn around the finger. Electronic device 219 may be a mobile phone and central processing and storage unit 220 may be one or more compute servers and data storage that are located at a remote location.

In such embodiments, the food intake tracking and feedback system may not use images to extract information about food intake and/or eating behavior. Alternatively, the food intake tracking and feedback system may leverage image capture capabilities that are available inside other devices, such as for example electronic device 219 or otherwise an electronic device that is external to electronic device 218.

Upon detection or prediction of the start of a food intake event, electronic device 218 may send a signal to electronic device 219, or to the electronic device that is otherwise housing the image capture capabilities to indicate that the actual, probable or imminent start of a food intake event has occurred. This may trigger electronic device 219, or the electronic device that is otherwise housing the image capture capabilities to enter a mode that will allow the user to capture an image with at least one less user step compared to its default mode or standby mode.

As an example, if the image capture capabilities are housed within electronic device 219 and electronic device 219 is a mobile phone, a tablet or a similar mobile device, electronic device 218 may send one or more signals to software that has been installed on electronic device 219 to indicate the actual, probable or imminent start of a food intake event. Upon receiving such signal or signals, the software on electronic device 219 may, among other things, take one or more of the following actions: unlock the screen of electronic device 219, open the Mobile Application related to the food intake and feedback subsystem, activate electronic device's 219 camera mode, push a notification to electronic device's 219 display to help a user with image capture, send a message to electronic device 218 to alert, remind and/or help a user with image capture.

After image capture by electronic device 219, or the electronic device that is otherwise housing the image capture capabilities, electronic device 219, or the electronic device that is otherwise housing the image capture capabilities, may give visual feedback to the user. Examples of visual feedback may include a pattern, shape or overlay showing recommended portion sizes, or a pattern, shape or overlay shade in one or more colors and/or with one or more brightness levels to indicate how healthy the food. Other examples are also possible.

Integration with Insulin Therapy System

One or more components of the food intake tracking and feedback system presented in this disclosure may interface to or be integrated with an insulin therapy system. In one specific example, upon detection of the start of a food intake event, feedback may be sent to the wearer to remind him or her to take a glucose level measurement and/or administer the proper dosage of insulin. One or more additional reminders may be sent over the course of the food intake event.

The food intake tracking and feedback system described in this disclosure, or components thereof may also be used by patients who have been diagnosed with Type I or Type II diabetes. For example, components described in the current disclosure may be used to detect automatically when a person starts eating or drinking. The detection of the start of a food intake event may be used to send a message to the wearer at or near the start of a food intake event to remind him or her to take a glucose level measurement and/or administer the proper dosage of insulin. The messaging may be automatic and stand alone. Alternatively, the system may be integrated with a wellness system or a healthcare maintenance and reminder system. The wellness system or the healthcare maintenance and reminder system may upon getting notified that the start of a food intake event has been detected send a message to the wearer. The wellness system or the healthcare maintenance and reminder system may receive additional information about the food intake event, such as the number of bites or sips, the estimated amount of food consumed, the duration of the meal, the pace of eating etc. The wellness system or the healthcare maintenance and reminder system may send additional messages to the wearer during or after the food intake event based on the additional information.

In another example, specific information about the content of the food intake may be used as an input, possibly combined with one or more other inputs, to compute the proper dosage of insulin to be administered. Information about food intake content may, among other things, include one or more of the following: amount of carbohydrates, amounts of sugars, amounts of fat, portion size, and molecular food category such as solids or liquids. Real-time, near real-time as well as historical information related food intake and eating patterns and behaviors may be included as inputs or parameters for computation of insulin dosages.

Other inputs that may be used as inputs or parameters to the algorithms that are used to compute insulin dosages may include, among other things, one or more of the following: age, gender, weight, historical and real-time blood glucose levels, historical and real-time activity, sleep and stress levels, vital sign information or other information indicative of the physical or emotional health of an individual.

Computation of insulin dosages may be done fully manually by the user, fully autonomously by a closed loop insulin therapy system or semi-autonomously where some or all of the computation is done by an insulin therapy system but some user intervention is still required. User intervention may, among other things, include activation of the insulin therapy computation unit, confirmation of the dosage, intervene or suspend insulin delivery in case user detects or identifies an anomaly.

In one specific embodiment, the food intake tracking and feedback system described herein may upon detection of the actual, probable or imminent start of a food intake event send one or more notifications to one or more caregivers of the user, in addition or instead of sending a notification to the user.

The user may upon the start of a food intake event, optionally prompted by a notification or signal from the system or from one his caregiver, take one or more images of the food or meal to one or more caregiver. The caregiver may analyze the images and send information about the content of the food back to the user. Information may, among other things, include estimation of certain macro-nutrient contents such as for example carbohydrates, sugars or fats, estimation of caloric value, advice on portion size.

In case the user is on an insulin therapy, additional information such as for example blood glucose level readings may also be sent to the caregiver, and information provided by a caregiver back to a user may also include advice on the insulin dosage to be administered and the timing when such insulin dosage or dosages should be administered. In certain implementations, the caregiver may not be a person but an artificial intelligence system.

Gesture Recognition

In the various systems described herein, accurate determination of gesture information can be important. For example, it would be useful to distinguish between a gesture connected with talking versus a gesture that signals the start of an eating event period. Some gestures might be easy to detect, such as the gesture of swinging an arm while walking, and thus measuring pace and number of steps, but other gestures might be more difficult, such as determining when a user is taking a bite of food, taking a drink, biting their nails, etc. The latter can be useful for assessing precursor behaviors. For example, suppose a health maintenance and reminder system detects a pattern of nail biting gestures followed five to ten minutes later with gestures associated with stress eating. The user might program their health maintenance and reminder system to signal them two minutes after nail biting so that the user becomes aware and more in tune with their behavior that would otherwise go unnoticed. For this to work, gesture detection should be accurate and reliable. This can be a problem where there is not a simple correlation between, say, movement of an accelerometer in a wearable bracelet and stress eating. Part of the reason for this is that the gestures that are of interest to the health maintenance and reminder system are not easily derived from a simple sensor reading.

Being able to determine whether a user is taking a bite of food or taking a sip of a drink, and being able to distinguish a bite from a sip, can be useful to provide proper weight management guidance. For example, a weight management monitoring and reminder system may monitor a user's food intake events from gestures. The weight management monitoring a reminder system may furthermore monitor a user's fluid intake events from gestures. Studies have shown that drinking sufficient water at the start or close to the start of a meal and further drinking sufficiently throughout the meal reduces food consumption and helps with weight loss. The user, the user's coach, the user's healthcare provider, or the provider of the weight management monitoring and reminder system may program the system such that it sends a reminder when a user starts eating without drinking or if it detects that the user is not drinking sufficiently throughout the meal. The system could also monitor the user's fluid intake throughout the day and be programmed to send reminders if the level of fluid intake does not meet the pre-configured level for a particular time of day. For this to work, the gesture detection should be reliable and accurate. This can be a problem where it is necessary to distinguish between gestures that have lots of similarities, such as for example distinguishing an eating gesture from a drinking gesture.

In various embodiments described herein, a processing system (comprising program code, logic, hardware, and/or software, etc.) takes in sensor data generated by electronic devices or other elements based on activities of a user. The sensor data might represent a snapshot of a reading at a specific time or might represent readings over a span of time. The sensors might be accelerometers, gyroscopes, magnetometers, thermometers, light meters and the like. From the sensor data, the processing system uses stored rules and internal data (such as information about what sensors are used and past history of use) to identify behavior events wherein a behavior event is a sequence of gestures and the gestures are determined from logical arrangement of sensor data having a start time, sensor readings, and an end time, as well as external data. The behavior event might be a high-level event, such as eating a meal, etc.

The determination of the boundaries of gestures, i.e., their start and end times, can be determined using methods described herein. Together, the data of a start time, sensor readings, and an end time is referred to herein as a gesture envelope. The gesture envelope might also include an anchor time, which is a data element defining a single time that is associated with that gesture envelope. The anchor time might be the midpoint between the start time and the end time, but might be based on some criteria based on the sensor data of the gesture envelope. An anchor time might be outside of the time span from the start time to the end time. Multiple anchor times per gesture are also possible.

A machine classifier, as part of the processing system (but can also be a separate computer system, and possibly separated by a network of some kind), determines from a gesture envelope what class of gesture might have resulted in that gesture envelope's sensor data and details of the gesture. For example, the machine classifier might output that the sensor data indicates or suggests that a person wearing a bracelet that includes sensors was taking a walk, talking a bite to eat, or pointing at something.

With such a system, if gestures can be accurately discerned, then a health maintenance and reminder system (or other system that uses gesture information) can accurately respond to gestures made. In an example described below, there is a set of sensors, or at least inputs from a set of sensors, coupled to a machine classification system that outputs gesture data from sensor readings, taking into account rules and stored data derived from training the machine classification system. A training subsystem might be used to train the machine classification system and thereby forming the stored data derived from training. Each of these components might use distinct hardware, or shared hardware, and can be localized and/or remote. In general, when a gesture is detected, a system can analyze that gesture, determine likely actual, probable or imminent activities and provide the user feedback with respect to those activities. For example, a vibration as a feedback signal to indicate that the user has previously set up the system to alert the user when the user has been drinking for a semi-continuous period of more than 45 minutes or that the user has reached their target for the amount of walking to be done in one session.

Figure 8:
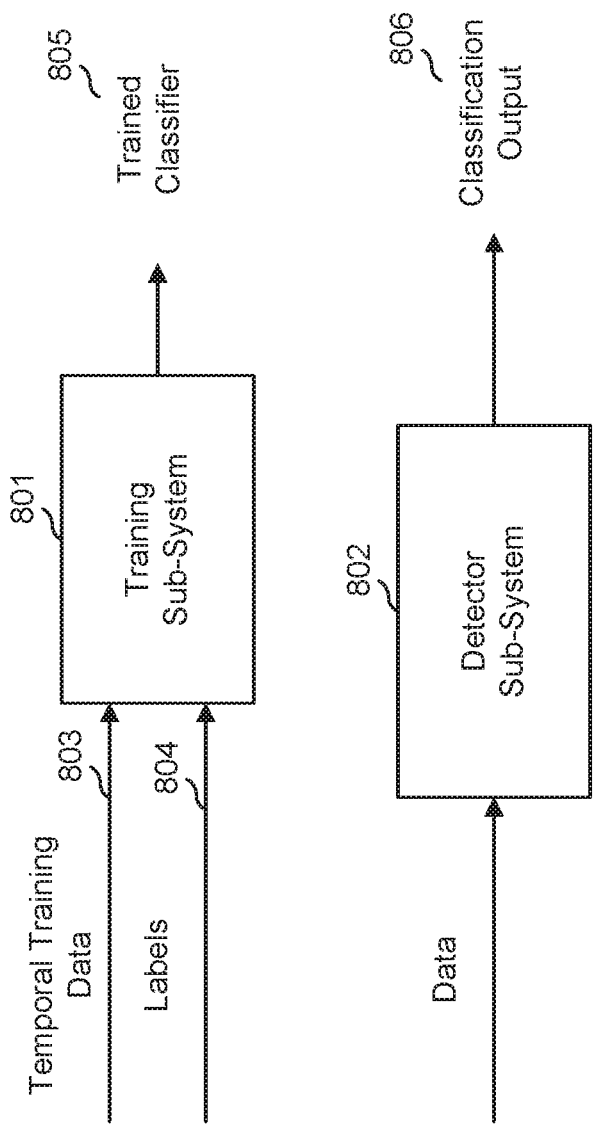
FIG. 8 shows an example of a machine classification system in accordance with at least one embodiment of the present disclosure.

FIG. 8 is an illustrative example of a typical machine classification system. The machine classification system of FIG. 8 includes a training subsystem 801 and a detector subsystem 802. In some embodiments of the present disclosure, the machine classification system may include additional subsystems or modified versions of the subsystems shown in FIG. 8. Training subsystem 801 uses training data inputs 803 and labels 804 to train trained classifier model 805. Labels 804 may have been assigned manually by a human or may have been generated automatically or semi-automatically. Trained classifier model 805 is then used in detector subsystem 802 to generate classification output 806 corresponding to a new unlabeled data input.

The stored sensor data includes temporal components. Raw sensor readings are tagged with their time of reading. The raw sensor data can be drawn from accelerometers, gyroscopes, magnetometers, thermometers, barometers, humidity sensors, ECG sensors and the like, and temporal data can come from other sources. Other examples of temporal sources might be audio, voice or video recordings.

Figure 9:
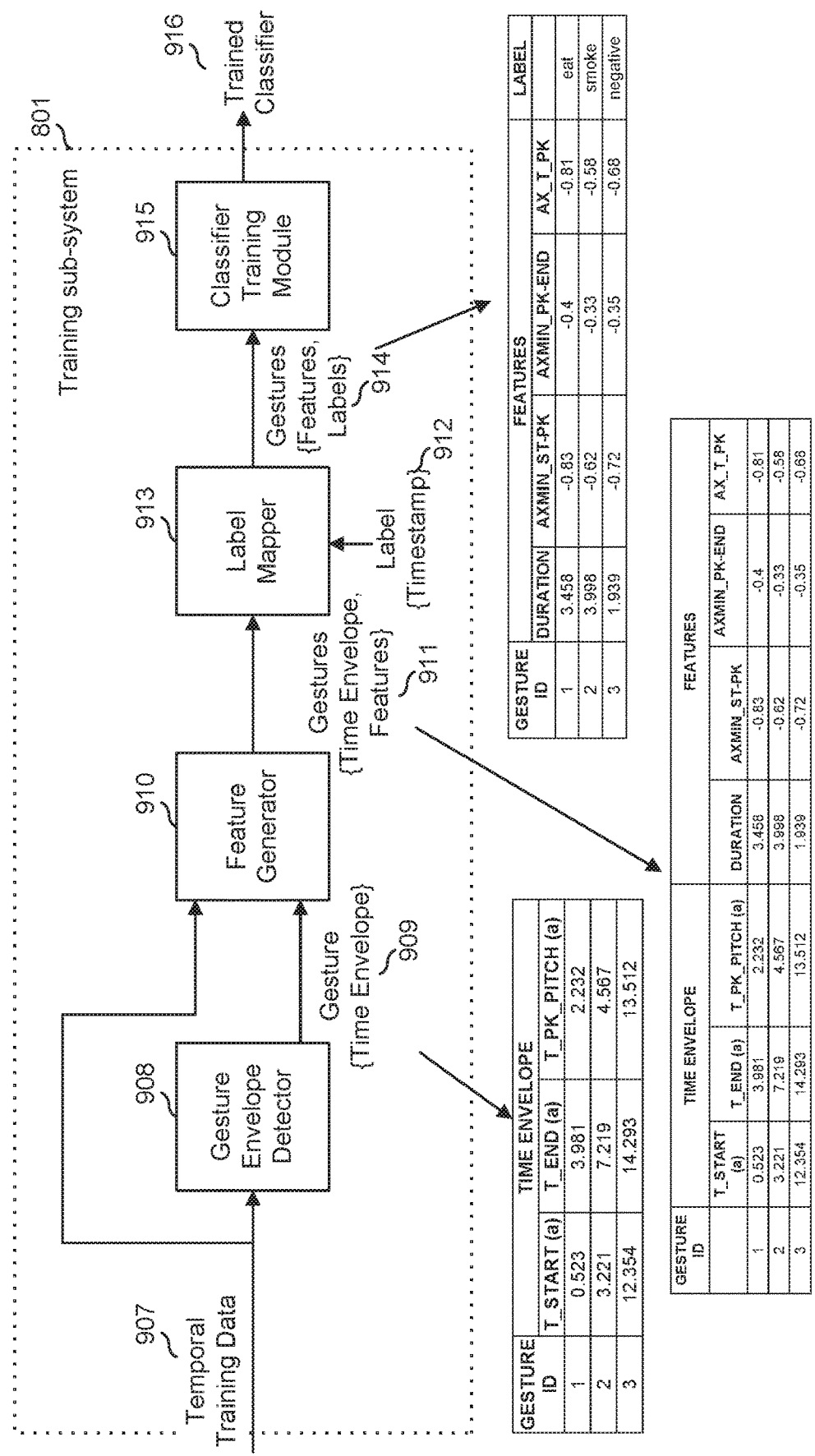
FIG. 9 shows an example of a machine classification training subsystem in accordance with at least one embodiment of the present disclosure.
Figure 10:
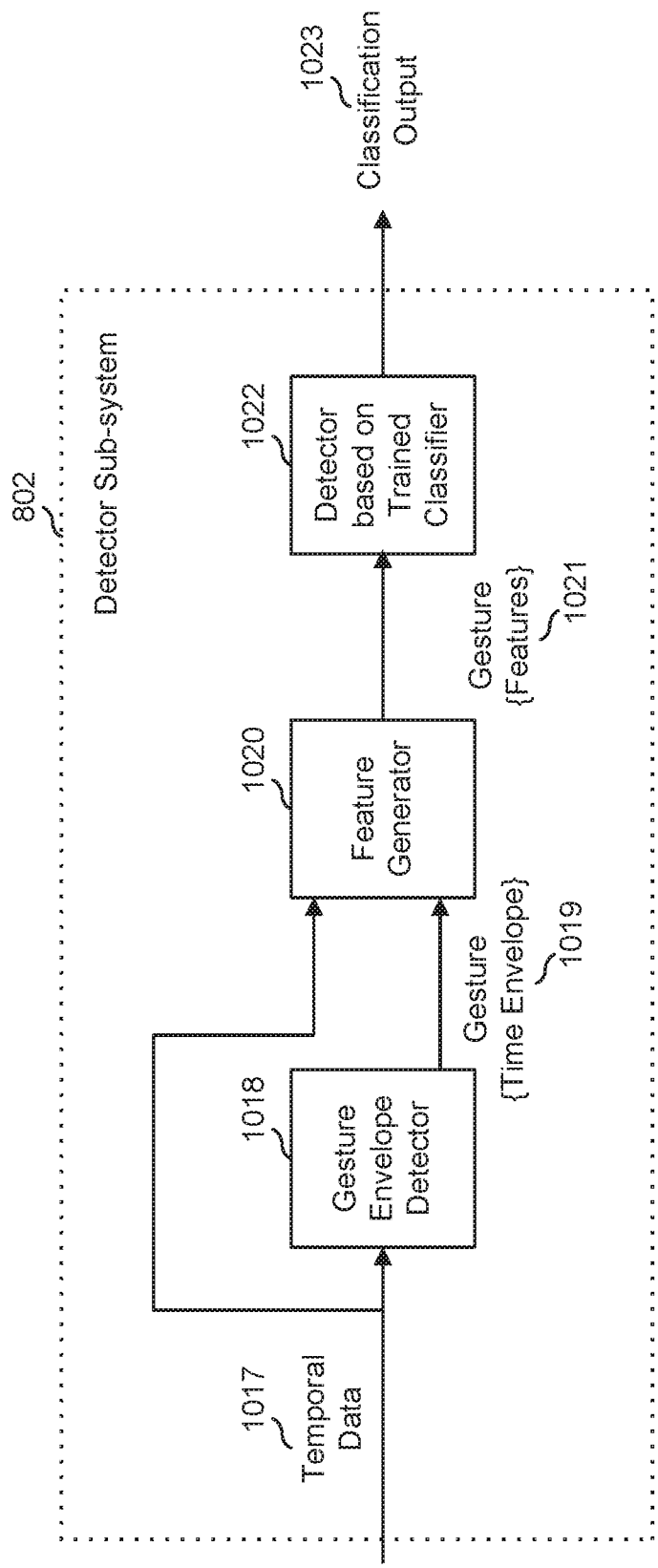
FIG. 10 shows an example of a machine classification detector subsystem in accordance with at least one embodiment of the present disclosure.

Illustrative examples of training subsystem 801 and detector subsystem 802 in accordance with at least one embodiment of the present disclosure are shown in FIG. 9 and FIG. 10 respectively. Temporal training data 907 and labels 912 are fed into classifier training subsystem of FIG. 8.

As explained in the examples herein, raw sensor data is processed to identify macro signature events. The macro signature events can delimit gestures that comprise sensor data over a period of time. The detector subsystem, or other system, can create a gesture envelope dataset comprising a start time, an end time, one or more anchor times, metadata and sensor data that occurred within that gesture's time envelope from the start time to the end time.

For example, in the case of a gesture recognition problem, the gesture envelope detector may identify specific time segments in the raw temporal data that are indicative of a possible gesture. The gesture envelope detector also generates a time envelope that specifies relevant times or segments of time within the gesture. Information included in the time envelope may among other things include start time of the gesture, end time of the gesture, time or times within the gesture that specify relevant gesture sub-segments, time or times within the gesture that specify relevant gesture anchor times (points) and possibly other metadata, and raw sensor data from within the gesture's time envelope.

As an example of other metadata, suppose historical patterns suggest that a wearer would have an eating session following a telephone call from a particular phone number. The electronic device can signal to the wearer about this condition, to provide conscious awareness of the pattern, which can help alter behavior if the wearer so decides.

Temporal training data 907 are fed into an gesture envelope detector 908. Gesture envelope detector 908 processes temporal training data 907 and identifies possible instances of gestures 909 and a corresponding gesturetime envelope from temporal training data 907. Temporal training data 907 may comprise motion sensor data and gesture envelope detector 908 may be processing the motion sensor data and identify gestures 909 based on changes in pitch angle. In one embodiment, gesture envelope detector 908 may detect the start of a gesture based on the detection of a rise in pitch angle above a specified value and the end of an event based on the pitch angle dropping below a specified value. Other start and end criteria are also possible. An example of anchor points that may be detected by gesture envelope detector 908 and specified by the gesture time envelope would be the time within the gesture segment when the pitch angle reaches a maximum. Other examples of anchor points are also possible.

Gesture envelope detector 908 may add additional criteria to further qualify the segment as a valid gesture. For example, a threshold could be specified for the peak pitch angle or the average pitch angle within the segment. In another example, minimum and/or maximum limits may be specified for the overall segment duration or for the duration of sub-segments within the overall segment. Other criteria are also possible. Hysteresis may be employed to reduce the sensitivity to noise jitters.

In other embodiments of the present disclosure, gesture envelope detector 908 may monitor other metrics derived from the input providing temporal training data 907 and use those metrics to detect gestures. Examples of other metrics include but are not limited to roll angle, yaw, first or higher order derivative, or first or higher order integration of motion sensor data. Temporal data may be or may include, data other than motion sensor data. In some embodiments of the present disclosure, an gesture envelope detector 908 may monitor and use multiple metrics to detect gestures or to specify the gesture time envelope.

Gestures 909 along with gesture time envelope information, combined with temporal training data 907 are fed into a feature generator module 910. Feature generator module 910 computes one or more gesture features using information from temporal training data 907, the gesture time envelope, or a combination of information from temporal training data 907 and the gesture time envelope. In some embodiments of the present disclosure, feature generator module 910 computes one or more gesture features from temporal training data 907 within or over a time segment that falls within the gesture time envelope. It is also possible that feature generator module 910 computes one or more gesture features from temporal training data 907 within or over a time segment that does not fall within or that only partially falls within the gesture time envelope, but that is still related to the gesture time envelope. An example would be an gesture feature that is computed from temporal training data 907 over a time period immediately preceding the start of the gesture time envelope or over a time period immediately following the end of the gesture time envelope.

In some embodiments, feature generator module 910 may create one or more features based on gesture time envelope information directly without using temporal training data 907. Examples of such features may include, but are not limited to, total duration of the gesture time envelope, elapsed time since a last prior gesture, a time until next gesture, or durations of specific sub-segments within the overall gesture time envelope or event time envelope.

In one embodiment, temporal training data 907 may be motion sensor data and features may include read of pitch, roll and/or yaw angles computed within, or over, one or more sub-segments that are inside or around the gesture time envelope. Features may also include minimum, maximum, mean, variance, first or higher order derivative, first or higher order integrals of various motion sensor data inputs computed within or over one or more sub-segments that are inside or around the gesture time envelope. Features may also include distance traveled along a specific sensor axis or in a specific direction computed within or over one or more sub-segments that are inside or around the gesture time envelope. Other features are also possible.

Temporal training data 907 may be, or may include, data other than motion sensor data, such as sensor signals from one or more of the sensors described herein. Sub-segments within or over which feature generator module 910 computes features may be chosen based on time points or time segments specified by the gesture time envelope. Sub-segments may also be chosen based on time points or time segments from multiple gesture envelopes, such as for example adjacent gestures or gestures that are may not be adjacent but are otherwise in close proximity.

Some embodiments may use a plurality of gesture envelope detectors, in parallel or otherwise. Parallel gesture envelope detectors may operate on a different subset of the sensor data, may use different thresholds or criteria to qualify gestures, etc. For example, in case of gesture recognition based on motion sensor data inputs, one gesture envelope detector may use the pitch angle, whereas a second, parallel gesture envelope detector may use roll angle. One of the gesture envelope detectors may be the primary gesture envelope detector, whereas one or more additional gesture envelope detectors may serve as secondary gesture envelope detectors. The Feature Generation logic may process gestures generated by the primary gesture envelope detector, but may gleam features derived using information from gesture time envelopes of nearby gestures (in time) obtained from one or more secondary, parallel envelope detectors.

Training data might comprise a plurality of gesture envelope datasets, each having an associated label representing a gesture (such as a selection from a list of gesture labels), provided manually, in a test environment, or in some other manner. This training data, with the associated labels, can be used to train the machine classifier, so that it can later process an gesture envelope of an unknown gesture and determine the gesture label most appropriately matching that gesture envelope. Depending on the classification method used, the training set may either be cleaned, but otherwise raw data (unsupervised classification) or a set of features derived from cleaned, but otherwise raw data (supervised classification).

Regardless of the classification method, defining the proper data boundaries for each label is important to the performance of the classifier. Defining the proper data boundaries can be a challenge in case of temporal problems, i.e., problems whereby at least one of the data inputs has a time dimension associated with it. This is particularly true if the time dimension is variable or dynamic and if features that are linked to specific segments of the variable time envelope or to the overall variable time envelope contribute materially to the performance of the classifier.

One example of such a temporal problem is gesture recognition, such as for example the detection of an eating or drinking gesture from raw motion sensor data. The duration of a bite or sip may vary person-to-person and may depend on the meal scenario or specifics of the foods being consumed. Examples of other gesture recognition problems are recognition of hand gestures related to smoking, dental hygiene, nail biting, nose picking, hair pulling, sign language, etc. In some variations, the system is used in a production environment to improve productivity.

The Feature Generation logic may also create features derived from combining outputs from multiple gesture envelope detector outputs. Examples include but are not limited to the elapsed time from a primary gesture to the nearest gesture from a parallel, secondary gesture envelope detector.

The output of the feature generator module 910 is a set of gestures 911 with corresponding time envelope and features. Before gestures 911 can be fed into Classifier Training module 915, labels 912 from the training dataset need to be mapped to their corresponding gesture. This mapping operation is performed by the Label Mapper module 913.

In some embodiments, the timestamps associated with labels 912 always fall within the time envelope of their corresponding gesture. In that case, the logic of Label Mapper module 913 can be a look up where the timestamp of each label is compared to the start and end time of each gesture time envelope and each label is mapped to the gesture for which the timestamp of the label is larger than the start time of the respective gesture time envelope and smaller than the end time of the respective gesture time envelope. Gestures for which there is no corresponding label may be labeled as "NEGATIVE," indicating it does not correspond to any labels of interest.

However, in other embodiments of the present disclosure, the timestamp of labels 912 may not always fall within an gesture time envelope. This may be due to the specifics of the procedures that were followed during the labeling process, timing uncertainty associated with the labeling process, unpredictability or variability in the actual raw data input, or an artifact of the gesture envelope detector logic. In such cases, the label mapper might be modified to adjust the boundaries of the gesture envelopes.

Gestures 914, characterized by features and a label, may then be fed into Classifier Training module 915 to produce a trained statistical model that can be used by the Detector subsystem. Classifier Training module 915 may use a statistical model such as a decision tree model, a K-nearest neighbors model, a Support Vector Machine model, a neural networks model, a logistic regression model or other model appropriate for a machine classification. In other variations, the structures of the tables and the data formats of the data used, as in FIG. 9, may vary and be different from that shown in FIG. 9.

FIG. 10 shows an illustrative example of a detector subsystem. As shown there, unlabeled temporal data 1017 is fed into the detector subsystem of FIG. 10. The detector subsystem includes gesture envelope detector logic 1018 and feature generator logic 1020. Functionally, gesture envelope detector logic 1018 used by the detector subsystem is similar to gesture envelope detector logic used by its corresponding training subsystem. Likewise, feature generator logic 1020 of the detector subsystem is functionally similar to feature generator module 910 of its corresponding training subsystem. In some embodiments, gesture envelope detector logic 1018 may monitor and use multiple metrics to detect gestures or to specify the gesture time envelope.

However, the implementation of gesture envelope detector logic 1018 and feature generator logic 1020 may be different in the training subsystem and its corresponding detector subsystem. For example, the detector subsystem may be implemented on hardware that is more power-constrained, in which case gesture envelope detector logic 1018 may need to be optimized for lower power operation compare to its counterpart used in the corresponding training subsystem. The detector subsystem may also have more stringent latency requirements compared to the training system. If this is the case, gesture envelope detector logic 1018 used in the detector subsystem may need to be designed and implemented for lower latency compared to its counterpart used in the corresponding training subsystem.

An output of feature generator logic 1020 is fed into feature generator logic 1020, which classifies the gesture based on the trained classifier module from its corresponding training subsystem. The Classification Output may include one or more labels. Optionally, Detector 1022 may also assign a confidence level to each label.

Classification on Combination of Temporal and Non-Temporal Data Inputs

Figure 11:
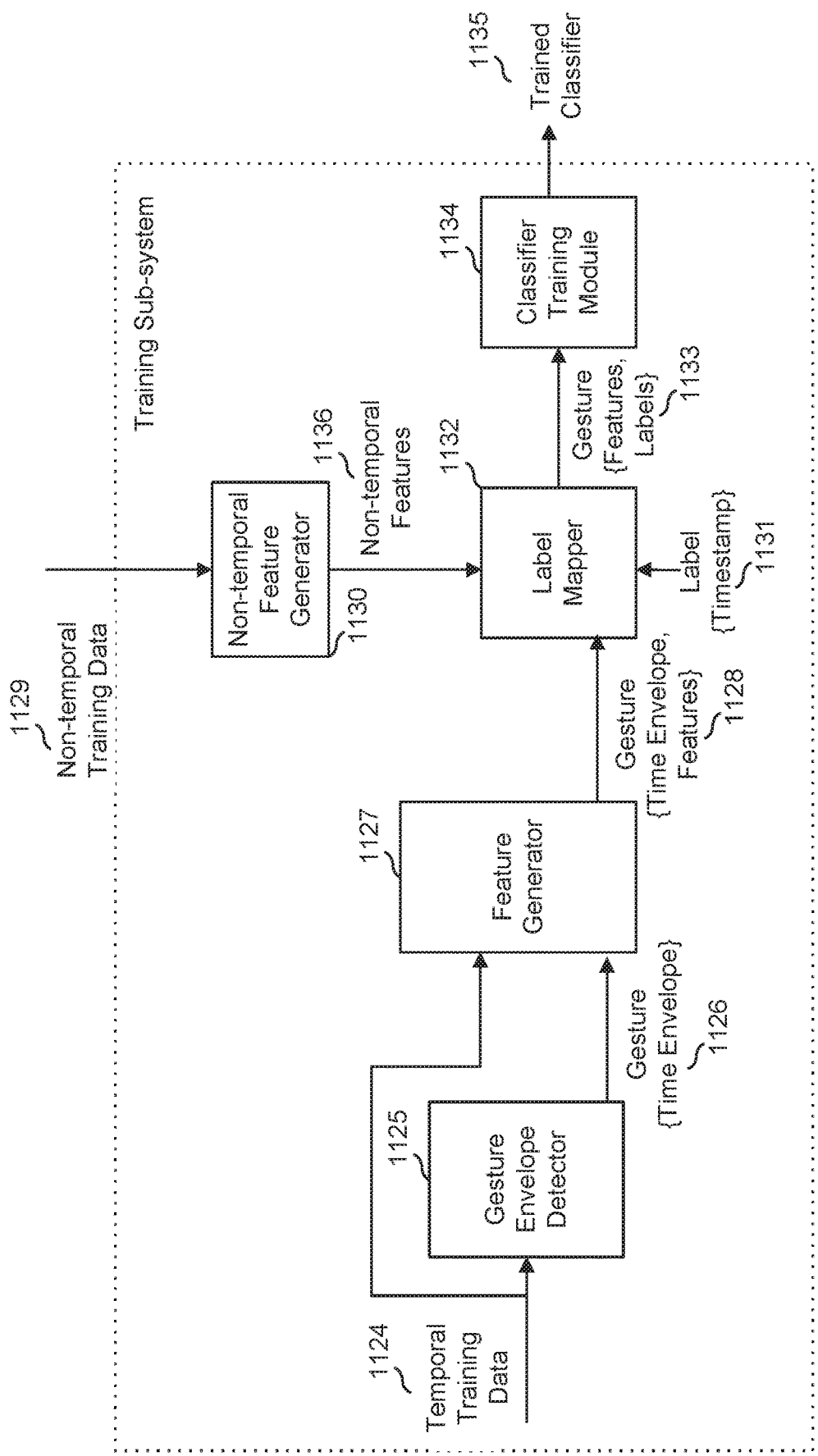
FIG. 11 shows an example of a machine classification training subsystem that uses, among other data, non-temporal data.

In another embodiment, inputs into the classification system may include a combination of temporal and non-temporal data. FIG. 11 is an illustrative example of a training subsystem in accordance with at least one embodiment of the present disclosure where at least some of the data inputs are temporal and at least some of the data inputs are non-temporal. Other implementations are also possible.

Non-temporal training data 1129 do not need to be processed by gesture envelope detector 1125 and feature generator Logic 1127. Non-temporal training data 1129 may be fed directly into the label mapper logic 1132 along with labels 1131. In some embodiments, non-temporal training data may be processed by a separate feature generator module, non-temporal feature generator module 1130, to extract specific non-temporal features of interest, which are then fed into Label mapper logic 1132. Label mapper logic 1132 may assign the labels 1131, along with non-temporal features 1136 that are attached to the label to gestures using methods similar to the methods for mapping labels to gestures that have been described herein.

Figure 12:
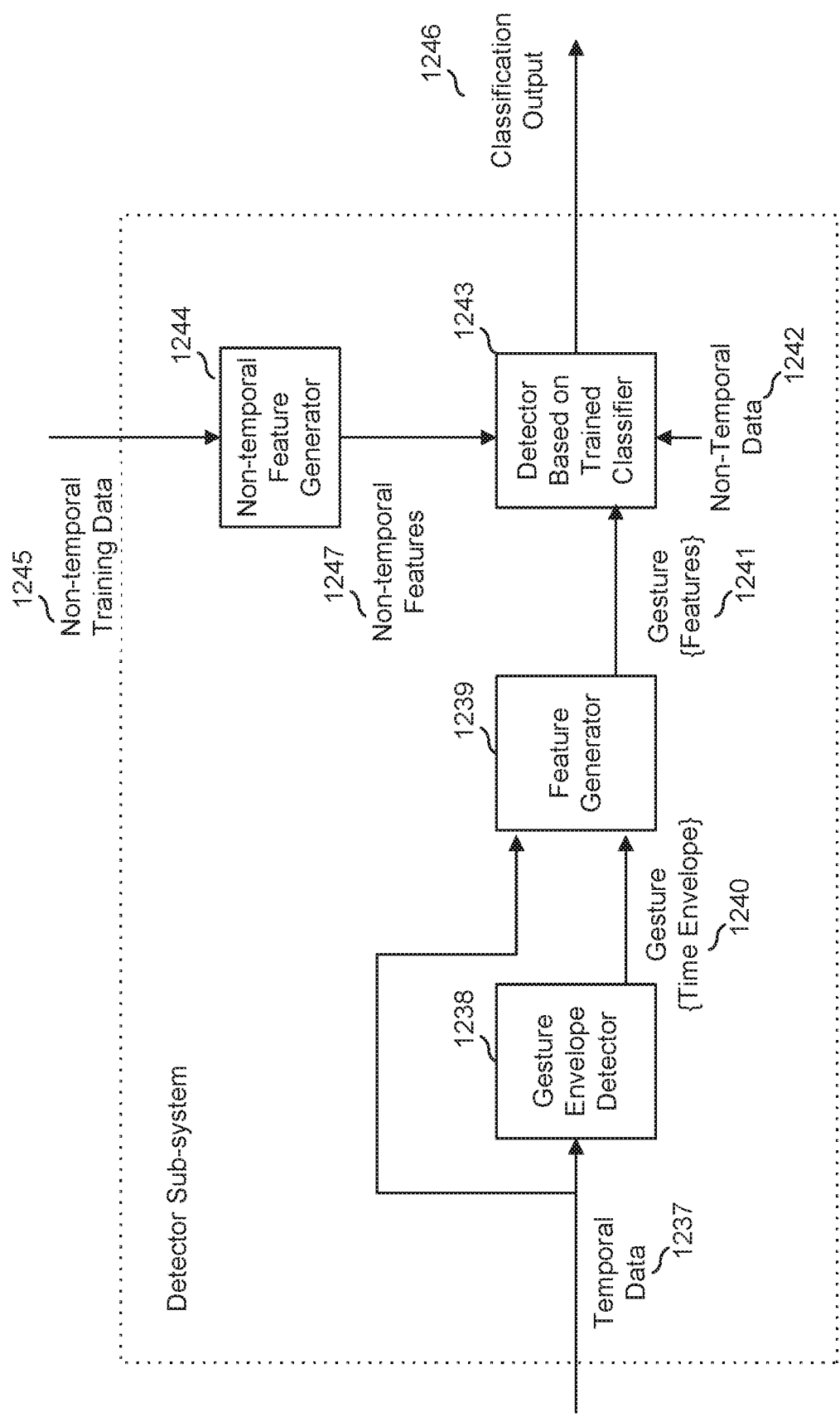
FIG. 12 shows an example of a machine classification detector subsystem that uses, among other data, non-temporal data.

FIG. 12 is an illustrative example of a classification detector subsystem in accordance with at least one embodiment of the present disclosure where at least some of the data inputs are temporal and at least some of the data inputs are non-temporal.

Unsupervised Classification of Temporal Data Inputs

In yet another embodiment of the present disclosure, deep learning algorithms may be used for machine classification. Classification using deep learning algorithms is sometimes referred to as unsupervised classification. With unsupervised classification, the statistical deep learning algorithms perform the classification task based on processing of the data directly, thereby eliminating the need for a feature generation step.

Figure 13:
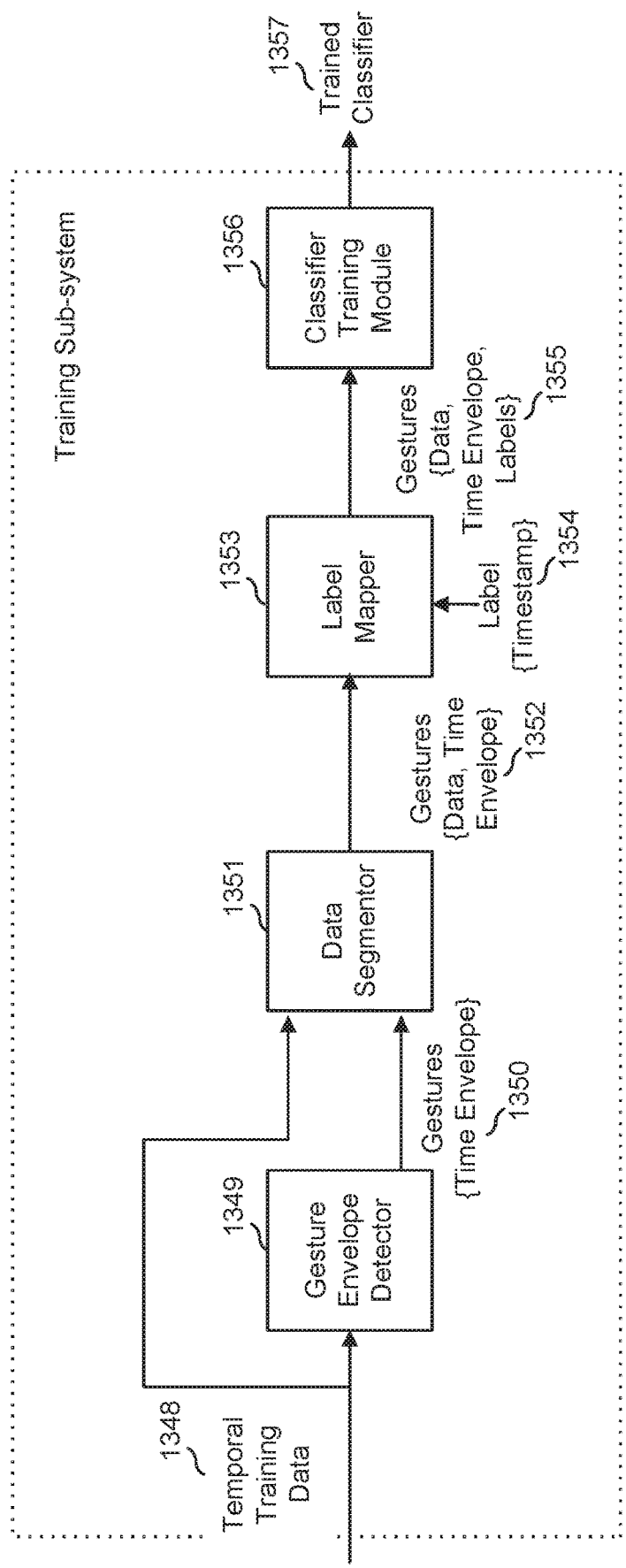
FIG. 13 shows an example of a training subsystem for an unsupervised classification system in accordance with at least one embodiment of the present disclosure.

FIG. 13 shows an illustrative example of a classifier training subsystem in accordance with at least one embodiment of the present disclosure where the classifier training module is based on statistical deep learning algorithms for unsupervised classification.

Gesture envelope detector 1349 computes gestures 1350 with corresponding gesture time envelopes from temporal training data 1348. Data segmentor 1351 assigns the proper data segment or data segments to each gesture based on information in the gesture time envelope. As an example, data segmentor 1351 may look at the start and end time information in the gesture time envelope and assign one or more data segments that correspond to the overall gesture duration. This is just one example. Data segments may be selected based on different segments or sub-segments defined by the gesture time envelope. Data segments could also be selected based on time segments that are outside of the gesture time envelope but directly or indirectly related to the gesture time envelope. An example could be selection of data segments corresponding to a period of time immediately preceding the start of the gesture time envelope or selection of data segments corresponding to a period of time immediately following the end of the gesture time envelope. Other examples of time segments that are outside the gesture time envelope but directly or indirectly related to the gesture time envelope are also possible.

Gestures including data segments, gesture time envelope information and labels are fed into classifier training module 1356. In some embodiments of the present disclosure, only a subset of the gesture time envelope information may be fed into classifier training module 1356. In some embodiments of the present disclosure, gesture time envelope information may be processed before it is being applied to classifier training module 1356. One example could be to make the time reference of the gesture time envelope align with the start of the data segment, rather than with the time base of the original temporal training data stream. Other examples are also possible. By adding time envelope information that further characterizes the data segments, the performance of the classifier training module may be improved.

For example, in case of gesture recognition of eating gestures based on motion sensor data inputs, feeding additional anchor time information such as the time when the pitch angle, roll or yaw reaches a maximum or minimum into the classifier training module can improve the performance of a trained classifier 1357 as trained classifier 1357 can analyze the training data and look for features and correlations specifically around said anchor times. Other examples of time envelope information that can be fed into the classifier training module are also possible.

Figure 14:
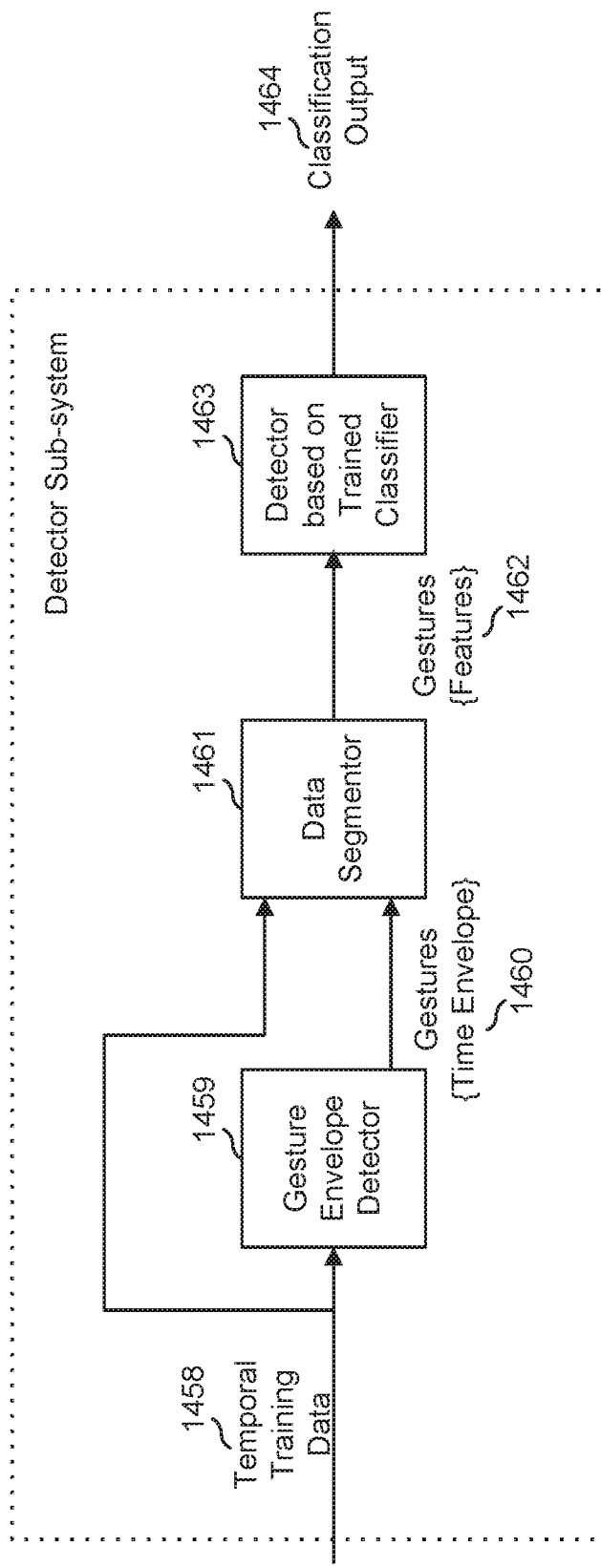
FIG. 14 shows an example of a detector subsystem for an unsupervised classification system in accordance with at least one embodiment of the present disclosure.

FIG. 14 shows an illustrative example of a classification detector subsystem in accordance with at least one embodiment of the present disclosure that could be used in combination with classification training subsystem of FIG. 13.

Classifier Ensemble

Figure 15:
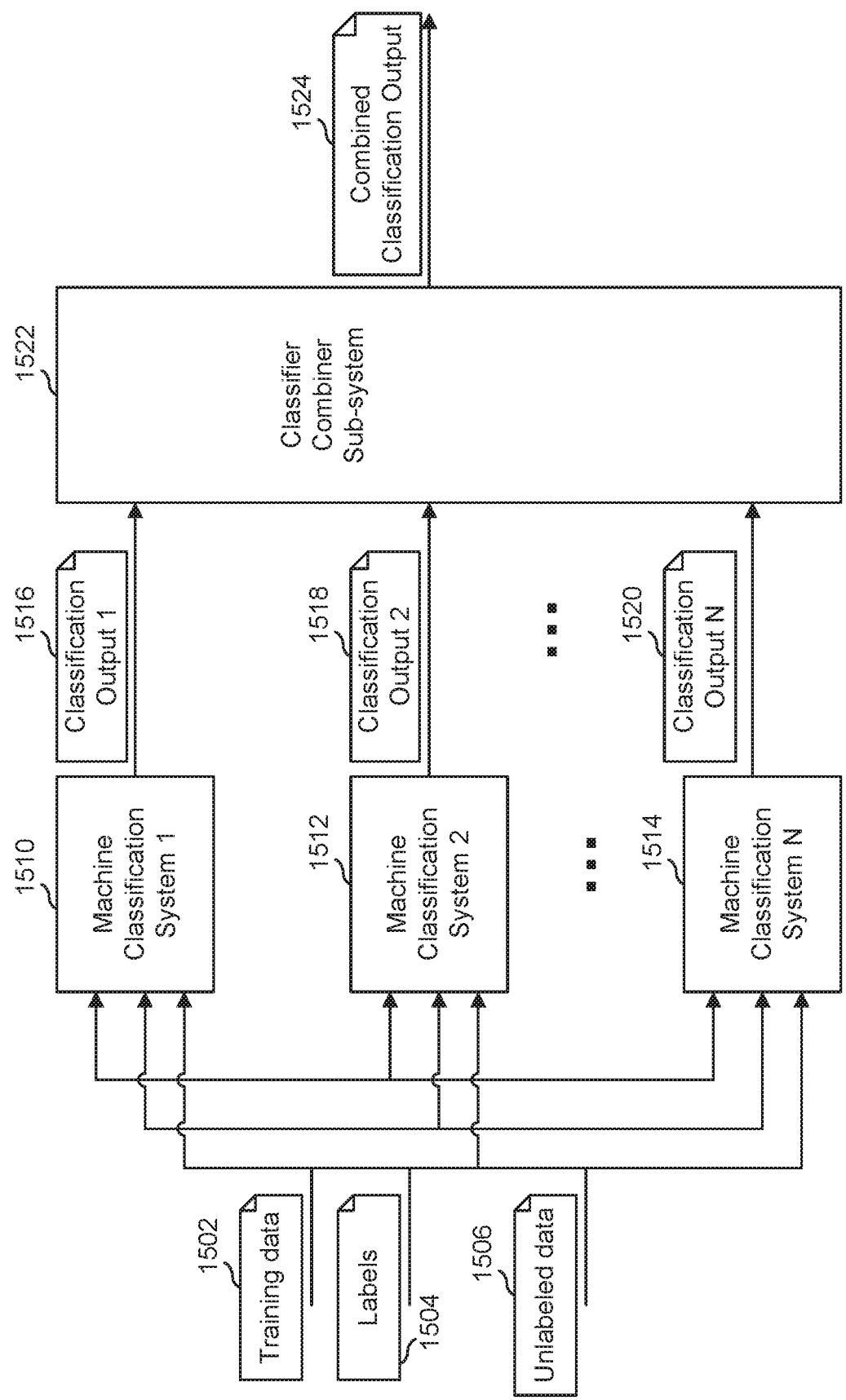
FIG. 15 shows an example of a classifier ensemble system.

In some embodiments, multiple parallel classification systems based on gesture envelope detection may be used. An example of a system with multiple parallel classifiers is shown in FIG. 15. The number of parallel classification systems may vary. Each classification system 1510, 1512, 1514 has its own training and detector sub-system and performs gesture envelope detection on a different subset of the training data 1502 and labels 1504 inputs to detect gestures, or may use different thresholds or criteria to qualify gestures. Consequently, each individual gesture envelope detector will generate an independent set of gestures each with different gesture time envelopes. The feature generator logic of each classification system creates features for the gestures created by its corresponding gesture envelope detector logic. The features may be different for each classification system. The classifier model used by each of the parallel classifiers may be the same or different, or some may be the same and others may be different. Since the gesture time envelopes and features used for training of each classifier model are different, the parallel classification systems will produce different Classification Outputs 1516, 1518, 1520.

The Classification Outputs 1516, 1518, 1520 of each classification system may be fed into Classifier Combiner sub-system 1522. Classifier Combiner sub-system 1522 may combine and weigh the Classification Outputs 1516, 1518, 1520 of the individual classification systems 1510, 1512, 1514 to produce a single, overall Classification result, Combined Classification Output 1524. The weighing may be static or dynamic. For example, in case of gesture recognition, certain classifiers may perform better at correctly predicting the gestures of one group of people, whereas other classifiers may perform better at correctly predicting the gestures of another group of people. Classifier Combiner sub-system 1522 may use different weights for different users or for different contextual conditions to improve the performance of the overall classifier ensemble. The trained system can then be used to process unlabeled data 1506.

Other examples of temporal problems include but are not limited to autonomous driving, driver warning systems (that alert the driver when dangerous traffic conditions are detected), driver alertness detection, speech recognition, video classification (security camera monitoring, etc.) and weather pattern identification.

Ignoring the temporal nature of the data inputs as well as any features that are linked to the temporal envelope of the data inputs can limit performance of the classifier and make the classifier non-suitable for classification tasks where a reliable detection depends on features that are inherently linked to segments of the variable time envelope or to the overall variable time envelope. Performance and usability can break down if a proper time period cannot be determined reliably, or where the time period varies from gesture-to-gesture, from person-to-person etc.

As described herein, improved methods frame temporal problems with a variable time envelope, so that information tied to the overall variable time envelope or to segments thereof can be extracted and included in the feature set used to train the classifier. The proposed improved methods improve performance and reduce the amount of training data needed since features can be defined relative to the time bounds of the variable time envelope, thereby reducing sensitivities to time and user variances.

In addition to finding time envelopes for gestures, the system can also find event time envelopes. In such an approach, the system might determine a gesture and a gesture envelope, but then do so for additional gestures and then define an event envelope, such as the start and end of an eating event.

Context to Improve Overall Accuracy

Figure 16:
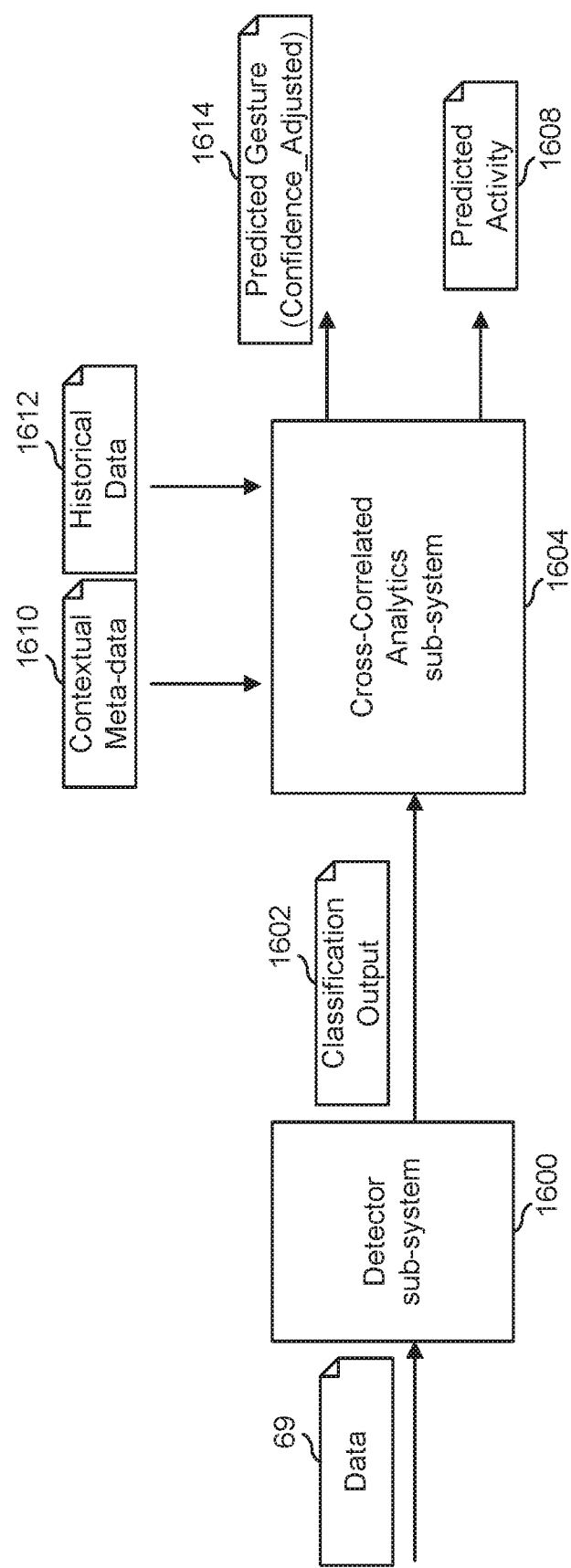
FIG. 16 shows an example of a machine classification system that includes a cross-correlated analytics sub-system.

FIG. 16 shows an example of a machine classification system that includes a Cross-correlated analytics sub-system. Classification output 1602 may be fed into cross-correlated analytics sub-system 1604. Cross-correlated analytics sub-system 1604 can make adjustments based one or more contextual clues to improve the accuracy. In the example of gesture recognition, an example of a contextual clue could be the proximity in time to other predicted gestures. For example, eating gestures tend to be grouped together in time as part of an eating activity such as a meal or a snack. As one example, Cross-correlated analytics sub-system 1604 could increase the confidence level that a predicted gesture is an eating gesture based on the confidence level and degree of proximity of nearby predictions.

In another embodiment, cross-correlated analytics sub-system 1604 may take individual predicted gestures 1614 from classification output 1602 as inputs and may cluster individual predicted gestures into predicted activities 1608. For example, cross-correlated analytics sub-system 1604 may map multiple bite gestures to an eating activity such as a snack or a meal. Likewise, cross-correlated analytics sub-system 1604 could map multiple sip gestures to a drinking activity. Other examples of activity prediction based on gesture clustering are also possible. Cross-correlated analytics sub-system 1604 may modify the confidence level of a predicted gesture based on the temporal spacing and sequence of predicted activities. As an example, Cross-correlated analytics sub-system 1604 could decrease the confidence level that a predicted gesture is an eating gesture if it is detected shortly following or amid a "brushing teeth" activity. In another example, Cross-correlated analytics sub-system 1604 could decrease the confidence level that a predicted gesture is a drinking gesture if it is detected during or shortly after a brushing teeth activity. In this case, Cross-correlated analytics sub-system 1604 could decide to increase the confidence level that the gesture is a rinsing gesture.

Cross-correlated analytics sub-system 1604 can adjust a classification output of a predicted gesture based on historical information 1612 or other non-gesture meta-data 1610 information such as location, date and time, other biometric inputs, calendar or phone call activity information. For example, Cross-correlated analytics sub-system 1604 may increase the confidence level that a predicted gesture is an eating gesture or a predicted activity is an eating activity if GPS coordinates indicate that the person is at a restaurant. In another example, Cross-correlated analytics sub-system 1604 may increase the confidence level that a predicted gesture is an eating gesture or a predicted activity is an eating activity if it occurs at a time of day for which past behavior indicates that the user typically engages in eating at this time of the day. In yet another example of the present disclosure, cross-correlated analytics sub-system 1604 may increase the confidence level that a predicted gesture is an eating gesture or that a predicted activity is an eating activity if the predicted gesture or predicted activity is preceding or following a calendar event or phone call conversation if past behavior indicates that the user typically eats preceding or following similar calendar events (e.g., with same attendee(s), at certain location, with certain meeting agenda, etc.) or phone call conversation (e.g., from specific phone number). While the above examples reference eating, it will be apparent to one skilled in the art that this could also be applied to gestures other than eating. In the general case, the machine classifier with cross-correlated analytics sub-system uses contextual clues, historical information and insights from proximity sensing in time to improve accuracy, where the specific contextual clues, historical information and insights from proximity sensing in time and how they are applied is determined by methods disclosed or suggested herein.

In some embodiments of the present disclosure, Classification Output 1602 may include additional features or gesture time envelope information. Cross-correlated analytics sub-system 1604 may process such additional features or gesture time envelope information to determine or extract additional characteristics of the gesture or activity. As an example, in one embodiment of the present disclosure, Cross-correlated analytics sub-system 1604 derives the estimated duration of the drinking gesture from the gesture time envelope and this information can be used by cross-correlated analytics sub-system 1604 or by one or more systems that are external to the machine classifier system to estimate the fluid intake associated with the drinking gesture.

In another embodiment, Cross-correlated analytics sub-system 1604 may derive the estimated duration of an eating gesture from the gesture time envelope and this information may be used by the cross-correlated analytics sub-system 1604 or by one or more systems that are external to the machine classifier system to estimate the size of the bite associated with the eating gesture. Cross-correlated analytics sub-system 1604 may combine the predicted drinking gestures with other sensor data to predict more accurately if someone is consuming a drink that contains alcohol and estimate the amount of alcohol consumed. Examples of other sensor data may include but are not limited to measuring hand vibration, heart rate, voice analysis, skin temperature, measuring blood, breath chemistry or body chemistry.

Detector sub-system 1600 may predict a specific eating or drinking method and cross-correlated analytics sub-system 1604 may combine the information obtained from detector sub-system 1600 about specifics of the eating or drinking method with additional meta-data to estimate the content, the healthiness or the caloric intake of the food. Examples of eating/drinking methods may include but are not limited to eating with fork, eating with knife, eating with spoon, eating with fingers, drinking from glass, drinking from cup, drinking from straw, etc.). Examples of meta-data may include but are not limited to time of day, location, environmental or social factors.

Interpretation

Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

What is claimed is:

1. A method of sensing wearer activity, including behavior events of a wearer of at least one electronic device, the method comprising:
    determining, using a processor, sensor readings, wherein at least one sensor reading is from an accelerometer of the at least one electronic device that measures movement of a body part of the wearer;
    determining a first gesture indicative of a potential behavior event from the sensor readings;
    determining, using the processor, a stored state, the stored state being a state from a set of states that includes an in-event state and an out-of-event state, wherein the processor processes gesture indications differently in the in-event state and in the out-of-event state;
    when in the out-of-event state, determining, using the processor and based on the first gesture, a start of at least one behavior event corresponding to the potential behavior event, based on detection of a single event with a confidence level above a predetermined confidence level or based on a sequence of two or more sensed gestures;
    activating, upon determining the start of the at least one behavior event, at least one sensor or component of a food intake tracking system;
    collecting, from the at least one sensor or component after activation, data or information related to the at least one behavior event;
    providing storage for event-specific parameters, initialized for the at least one behavior event;
    determining, when in the in-event state, a sequence of gestures related to the at least one behavior event; and
    deriving the event-specific parameters about the at least one behavior event from the sequence of gestures.

2. The method of claim 1, wherein the event-specific parameters include one or more of a timestamp relative to a start of the at least one behavior event, a pace related to the at least one behavior event, and/or a measure of an amount of an activity associated with the at least one behavior event.

3. The method of claim 2, wherein the timestamp is equal to the start of the at least one behavior event.

4. The method of claim 1, wherein the body part of the wearer is an arm, hand, and/or wrist of the wearer of the at least one electronic device.

5. The method of claim 1, wherein determining sensor readings comprises receiving signals from one or more of the accelerometer and additional sensors for detecting a start of the at least one behavior event and wherein the additional sensors include a gyroscope.

6. The method of claim 1, further comprising training a learning engine to predict an occurrence of the at least one behavior event based on tracking of one or more of gender, age, weight, social-economic status, timing information about the at least one behavior event, information about a location of the at least one behavior event, and vital signs information.

7. The method of claim 6, further comprising:
    identifying, using the learning engine, signatures of event time envelopes, thereby delimiting an event time envelope;
    identifying, using limits of the event time envelope, gestures within the event time envelope; and
    deriving, from the gestures, the at least one behavior event.

8. The method of claim 1, further comprising:
    storing a learned dataset in a memory storage, wherein the learned dataset comprises data usable to detect a type of gesture based on training examples; and
    determining, using a classifier trained on the learned dataset comprising data records related to prior gestures of the wearer or other users, possible gestures of the wearer taking into account outputs of the classifier, whereby the classifier can be used in a behavior event detection system to detect a start of the at least one behavior event, wherein the learned dataset comprises data related to one or of sleep pattern, stress level, daily interactions, and recent activities.

9. The method of claim 1, wherein the at least one behavior event is a food intake event.

10. A method of sensing wearer activity, including at least one food intake event, using at least one electronic device worn by a wearer, the method comprising:
    determining, using a processor, sensor readings, wherein at least one sensor reading is from an accelerometer of the at least one electronic device that measures movements of a body part of the wearer;

determining a first gesture indicative of a potential food intake event from the sensor readings;

activating, upon determining the first gesture indicative of the potential food intake event, at least one sensor or component of a food intake tracking system;

collecting, from the at least one sensor or component after activation, data or information related to the potential food intake event;

providing storage for event-specific parameters, initialized for an identified food intake event and an indication of whether the first gesture indicated that the at least one electronic device is in an in-event state, corresponding to the potential food intake event being the identified food intake event;

determining, when in the in-event state, a sequence of gestures related to the identified food intake event;

deriving the event-specific parameters about the identified food intake event from the sequence of gestures; and detecting at least one of a cadence and/or a duration of gestures and computing therefrom a size of a food intake step.

11. The method of claim 10, wherein the cadence corresponds to a function of one or more of a rotation, speed, acceleration, and/or deceleration of an arm, hand, and/or wrist.

12. The method of claim 10, wherein the identified food intake event is a drinking event and the food intake step is a sip.

13. The method of claim 10, further comprising computing, from a plurality of food intake steps, a total estimated consumption.

14. The method of claim 13, wherein the identified food intake event is a drinking event, the food intake step is a sip, and the total estimated consumption is an estimated hydration intake.

15. The method of claim 13, wherein the total estimated consumption is compared to a food intake portion target.

16. The method of claim 15, wherein the identified food intake event is a drinking event, the food intake step is a sip, and the food intake portion target is a hydration target.

17. The method of claim 10, wherein computing the size of the food intake step comprises:

measuring time periods in which a hand of the wearer, a utensil or a fluid container was near a mouth of the wearer; and using values of the time periods as an input to generate an estimate size of the food intake step.

18. The method of claim 17, wherein the estimate size is of a sip and a sip size is estimated from at least an amount of rotation of a wrist of the wearer.

19. The method of claim 17, further comprising computing a time corresponding to a peak of a pitch of a hand movement of the hand to the mouth.

20. The method of claim 10, wherein the event-specific parameters include one or more of a timestamp relative to a start of the identified food intake event, a pace related to the identified food intake event, and/or a measure of an amount of food consumed in the identified food intake event.

21. The method of claim 10, further comprising training a learning engine to predict an occurrence of the identified food intake event based on tracking of one or more of gender, age, weight, social-economic status, timing information about the identified food intake event, information about a location of the identified food intake event, vital signs information, and hydration level information.

22. The method of claim 10, further comprising estimating one or more of a duration of the identified food intake event, a bite count, a sip count, an eating pace, or a drinking pace.

23. The method of claim 10, further comprising:

identifying, using a learning engine, signatures of event time envelopes, thereby delimiting an event time envelope;

identifying, using limits of the event time envelope, gestures within the event time envelope; and deriving, from the gestures, the identified food intake event.

24. A method of sensing wearer activity, including at least one behavior event, using at least one electronic device worn by a wearer, the method comprising:

determining, using a processor, sensor readings, wherein at least one sensor reading is from an accelerometer of the at least one electronic device that measures movement of an arm of the wearer;

determining a first gesture indicative of a potential event from the sensor readings;

determining, using the processor, a stored state, the stored state being a state from a set of states that includes an in-event state and an out-of-event state;

determining, using the processor and based on the first gesture, a start of the at least one behavior event;

sending, upon detection of the start of the at least one behavior event, an activation signal to an image capture device to perform an action related to facilitating a capture of an image related to the at least one behavior event;

collecting, from the image capture device after activation, a captured image related to the at least one behavior event;

providing storage for event-specific parameters, initialized for the behavior event;

determining, when in the in-event state, a sequence of gestures related to the behavior event, using the processor; and deriving the event-specific parameters about the behavior event from the sequence of gestures, the event-specific parameters including a timestamp relative to the start of the behavior event.

25. The method of claim 24, wherein the action related to facilitating the capture of the image comprises capturing the image.

26. The method of claim 24, wherein the action related to facilitating the capture of the image comprises opening a camera app.

27. The method of claim 24, wherein the action related to facilitating the capture of the image comprises unlocking an input screen of the image capture device.

28. The method of claim 24, wherein the image capture device is a smartphone.

29. The method of claim 24, wherein the at least one behavior event is one food intake event.

30. The method of claim 24, further comprising training a learning engine to predict an occurrence of the at least one behavior event based on tracking of one or more of gender, age, weight, social-economic status, timing information about the at least one behavior event, information about a location of the at least one behavior event, vital signs information, and hydration level information.

* * * * *